United States Patent
Stults et al.

(10) Patent No.: US 9,481,690 B2
(45) Date of Patent: Nov. 1, 2016

(54) POLYMORPHS OF 2-(4-(2-(1-(ISOPROPYL-3-METHYL-1H-1,2,4,TRIAZOL-5-YL)-5,6-DIHYDROBENZO[F]IMIDAZO[1,2-D][1,4]OXAZEPIN-9-YL)-1H-PYRAZOL-1-YL)-2-METHYLPROPANAMIDE, METHODS OF PRODUCTION, AND PHARMACEUTICAL USES THEREOF

(71) Applicant: Genentech, Inc., South San Francisco, CA (US)

(72) Inventors: Jeffrey Stults, El Granada, CA (US); Travis Remarchuk, San Francisco, CA (US); Frederic St-Jean, San Francisco, CA (US)

(73) Assignee: Genentech, Inc., South San Francisco ( * ) Notice: Subject to any disclaimer, the term of this patent is extended or adjusted under 35 U.S.C. 154(b) by 0 days.

(21) Appl. No.: 14/991,658

(22) Filed: Jan. 8, 2016

(65) Prior Publication Data
US 2016/0222027 A1   Aug. 4, 2016

Related U.S. Application Data

(63) Continuation of application No. 14/570,019, filed on Dec. 15, 2014, now Pat. No. 9,266,903.

(60) Provisional application No. 61/916,657, filed on Dec. 16, 2013.

(51) Int. Cl.
| | |
|---|---|
| *C07D 498/04* | (2006.01) |
| *A61K 31/553* | (2006.01) |
| *C07D 498/06* | (2006.01) |
| *A61K 45/06* | (2006.01) |

(52) U.S. Cl.
CPC ........... *C07D 498/04* (2013.01); *A61K 31/553* (2013.01); *A61K 45/06* (2013.01); *C07D 498/06* (2013.01); *C07B 2200/13* (2013.01)

(58) Field of Classification Search
CPC ..................................................... C07D 498/06
USPC .......................................................... 514/183
See application file for complete search history.

(56) References Cited

U.S. PATENT DOCUMENTS

| | | | |
|---|---|---|---|
| 8,242,104 B2 * | 8/2012 | Blaquiere | ............ C07D 498/04 514/211.1 |
| 8,343,955 B2 | 1/2013 | Blaquiere et al. | |
| 8,586,574 B2 | 11/2013 | Blaquiere et al. | |
| 8,785,626 B2 | 7/2014 | Blaquiere et al. | |

FOREIGN PATENT DOCUMENTS

| | | |
|---|---|---|
| WO | 2011/036280 A1 | 3/2011 |
| WO | 2014/140073 A1 | 9/2014 |

OTHER PUBLICATIONS

Caira, "Crystalline Polymorphism of Organic Compounds" Topics in Current Chemistry, Springer, Berlin, DE 198:163-208 (Jan. 1, 1998).

Ndubaku et al., "Discovery of 2-{3-[2-(1-Isopropyl-3-methyl-1H-1,2-4-triazol-5-yl)-5,6-dihydrobenzo[f]imidazo[1,2-d]oxazepin-9-yl]-1H-pyrazol-1-yl}-2-methylpropanamide (GDC-0032): A β—Sparing Phosphoinositide 3-Kinase Inhibitor with High Unbound Exposure and Robust in Vivo Antitumor Activity" J. Med. Chem. 56:4597-4610 ( 2013).

PCT ISR and Written Opinion for PCT/EP2014/077666.

\* cited by examiner

*Primary Examiner* — Yong Chu
*Assistant Examiner* — Ana Z Muresan

(57) ABSTRACT

The present invention relates to crystalline polymorphs of (2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (GDC-0032, taselisib), methods of use, and processes of preparing thereof.

4 Claims, 19 Drawing Sheets

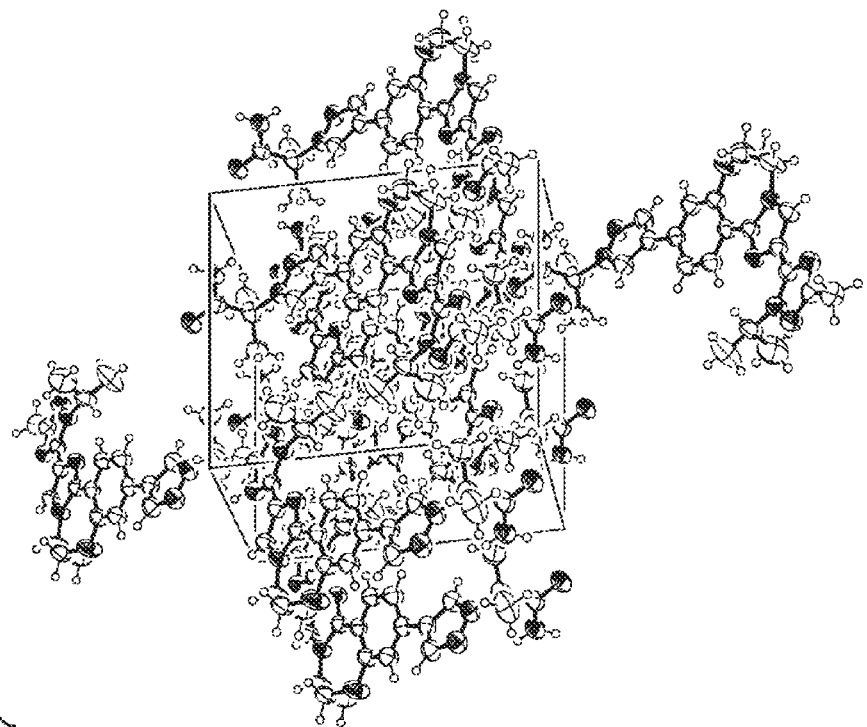
FIG. 4 — Packing Diagram of GDC-0032 Viewed Down the Crystallographic (100) Plane
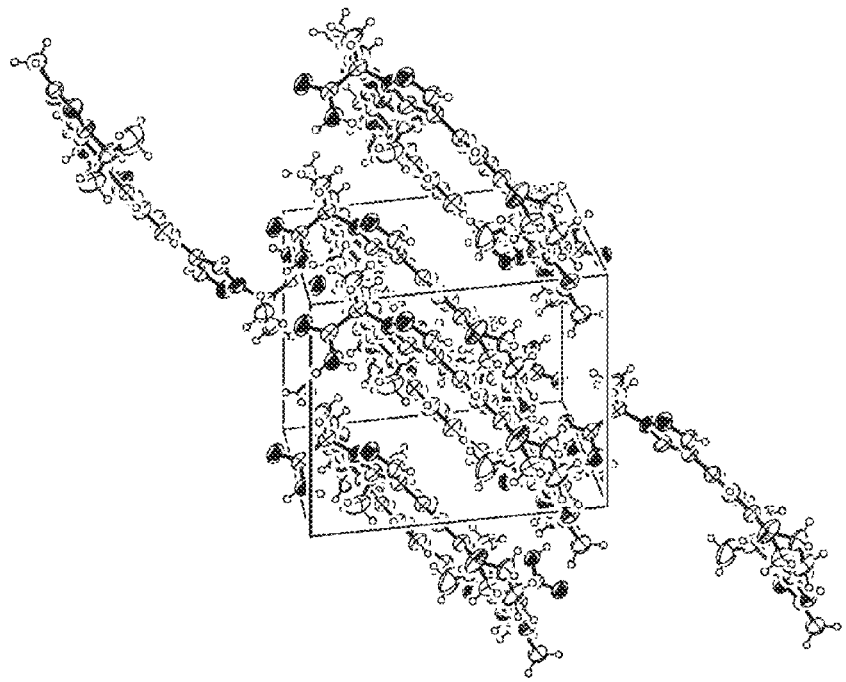
FIG. 5 — Packing Diagram of GDC-0032 Viewed Down the Crystallographic (010) Plane

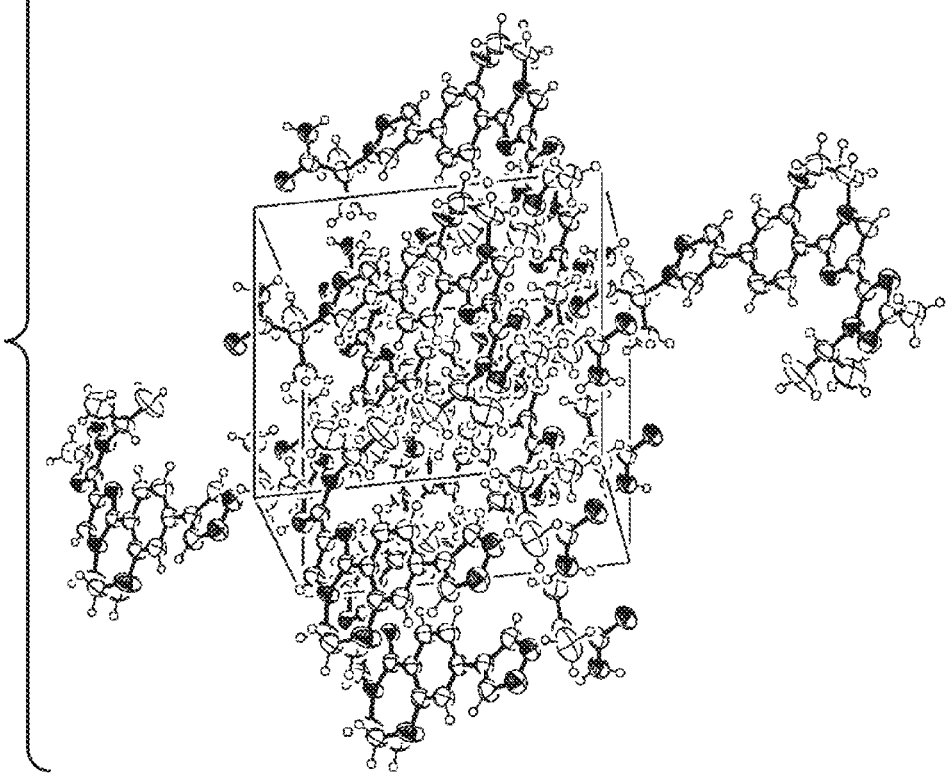
FIG. 6 Packing Diagram of GDC-0032 Viewed Down the Crystallographic C Axis Hydrogen Bonding in GDC-0032 Denoted by Elongated Lines Apparent Π-Stacking Interaction in GDC-0032

POLYMORPHS OF 2-(4-(2-(1-(ISOPROPYL-3-METHYL-1H-1,2,4,TRIAZOL-5-YL)-5,6-DIHYDROBENZO[F] IMIDAZO[1,2-D][1,4]OXAZEPIN-9-YL)-1H-PYRAZOL-1-YL)-2-METHYLPROPANAMIDE, METHODS OF PRODUCTION, AND PHARMACEUTICAL USES THEREOF

CROSS REFERENCE TO RELATED APPLICATIONS

This non-provisional application filed under 37 CFR §1.53(b) is a continuing application of U.S. Ser. No. 14/570,019 having a Filing Date of 15 Dec. 2014, and which claims the benefit of priority to U.S. Provisional Application Ser. No. 61/916,657 filed on 16 Dec. 2013, which are incorporated by reference in their entirety.

FIELD OF THE INVENTION

The invention relates to polymorph forms of a PI3K inhibitor compound GDC-0032, named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide. The invention also relates to processes to obtain polymorph forms of GDC-0032 and methods of using pharmaceutical compositions of polymorph forms of GDC-0032 for in vitro, in situ, and in vivo diagnosis or treatment of mammalian cells, or associated pathological conditions

BACKGROUND OF THE INVENTION

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al (2008) J. Med. Chem. 51:5522-5532; Yaguchi et al (2006) Jour. of the Nat. Cancer Inst. 98(8):545-556). The PI3K-PTEN-AKT signaling pathway is deregulated in a wide variety of cancers (Samuels Y, Wang Z, Bardellil A et al. High frequency of mutations of the PIK3CA gene in human cancers. (2004) Science; 304 (5670):554; Carpten J, Faber A L, Horn C. "A transforming mutation in the pleckstrin homology domain of AKT1 in cancer" (2007) Nature; 448:439-444).

GDC-0032, also known as taselisib, RG7604, or the IUPAC name: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, has potent PI3K activity (Ndubaku et al (2013) J. Med. Chem. 56(11):4597-4610; WO 2013/182668; WO 2011/036280; U.S. Pat. No. 8,242,104; U.S. Pat. No. 8,343,955) and is being studied in patients with locally advanced or metastatic solid tumors (Juric et al "GDC-0032, a beta isoform-sparing PI3K inhibitor: Results of a first-in-human phase Ia dose escalation study", 2013 (April 7) Abs LB-64 American Association for Cancer Research Annual Meeting).

Multiple crystal forms with different solid state properties of a drug substance can exhibit differences in bioavailability, shelf life and behavior during processing. Powder X-ray Diffraction is a powerful tool in identifying different crystal phases by their unique diffraction patterns The pharmaceutical industry is often confronted with the phenomenon of multiple polymorphs of the same crystalline chemical entity. Polymorphism is often characterized as the ability of a drug substance to exist as two or more crystalline phases that have different arrangements and/or conformations of the molecules in the crystal lattices giving the crystals different physicochemical properties. The ability to be able to manufacture the selected polymorphic form reliably is a key factor in determining the success of the drug product.

Regulatory agencies worldwide require a reasonable effort to identify the polymorphs of the drug substance and check for polymorph interconversions. Due to the often unpredictable behavior of polymorphs and their respective differences in physicochemical properties, consistency in manufacturing between batches of the same product must be demonstrated. Proper understanding of the polymorph landscape and nature of the polymorphs of a pharmaceutical will contribute to manufacturing consistency.

Knowledge of crystal structure at the atomic level and intermolecular interactions offer important information to establish absolute configuration (enantiomers), phase identification, quality control, and process development control and optimization. X-ray Diffraction is widely recognized as a reliable tool for the crystal structure analysis of pharmaceutical solids and crystal form identification.

Availability of a single crystal of the drug substance is preferred due to the speed and accuracy of the structure determination. However, it is not always possible to obtain a crystal of suitable size for data collection. In those cases the crystal structure can be solved from X-ray powder diffraction data obtained by measurements at ambient conditions and/or at variable temperature or humidity.

SUMMARY OF THE INVENTION

The invention relates to polymorph forms of the PI3K inhibitor I (taselisib, GDC-0032, RG7604, CAS Reg. No. 1282512-48-4, Genentech, Inc.), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, having the structure:

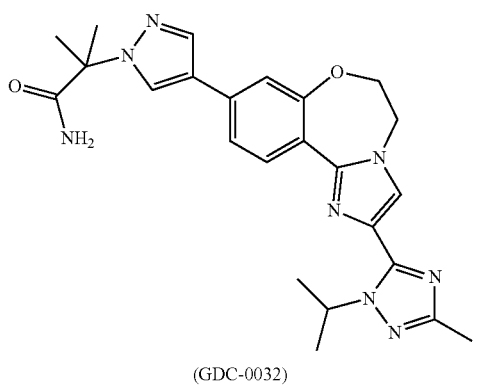

(GDC-0032)

and stereoisomers, geometric isomers, tautomers, and pharmaceutically acceptable salts thereof.

An aspect of the invention is a pharmaceutical composition of a polymorph form of taselisib.

An aspect of the invention is a method of treating a hyperproliferative disorder in a mammal with a polymorph form of taselisib.

An aspect of the invention is a process for preparing a crystalline polymorph of taselisib.

BRIEF DESCRIPTION OF THE DRAWINGS

FIG. 4 shows a Packing diagram of GDC-0032 viewed down the crystallographic a axis.

FIG. 5 shows a Packing diagram of GDC-0032 viewed down the crystallographic b axis.

FIG. 6 shows a Packing diagram of GDC-0032 viewed down the crystallographic c axis.

DETAILED DESCRIPTION OF EMBODIMENTS OF THE INVENTION

Figure 1:
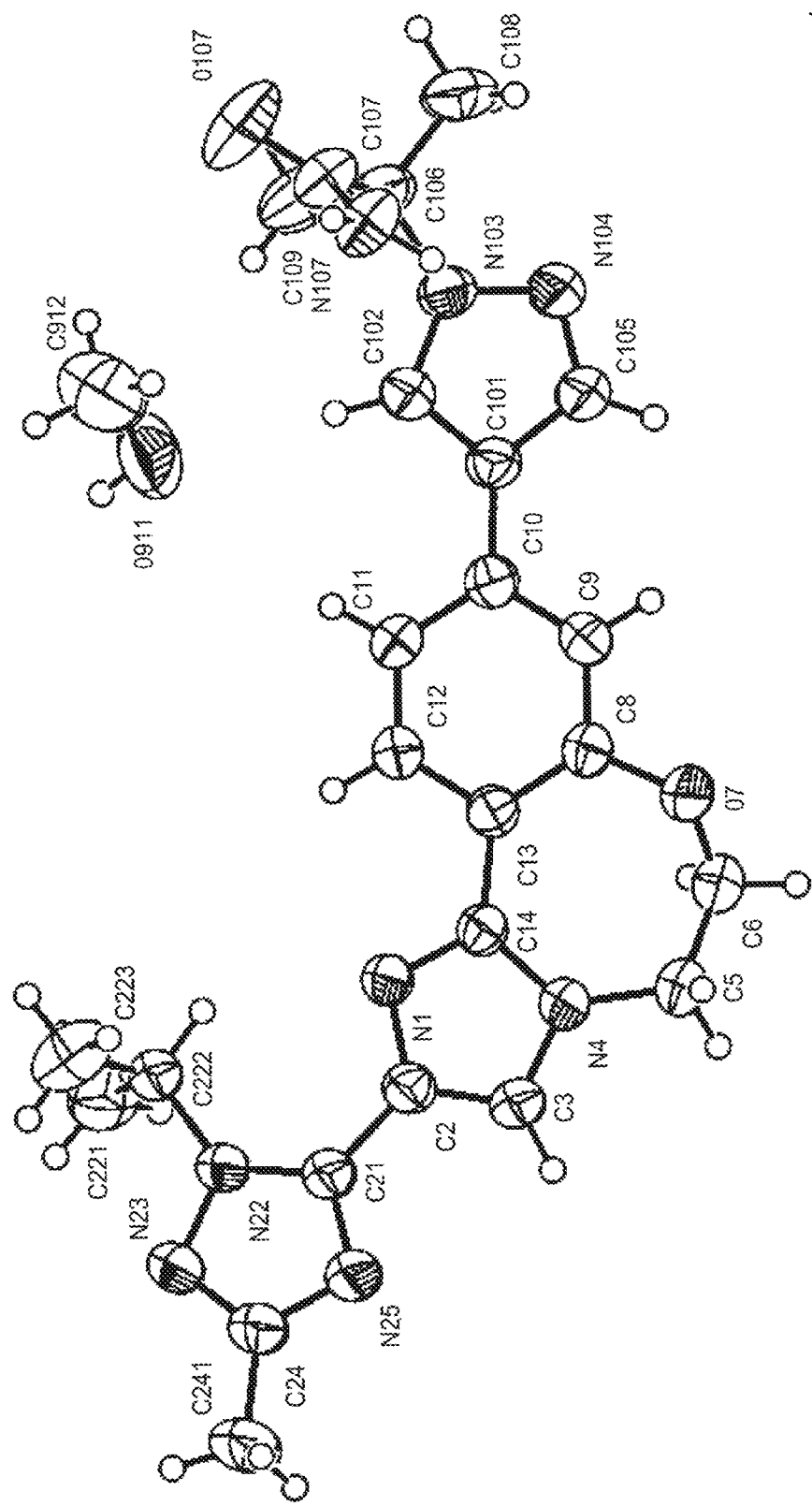
FIG. 1 shows an ORTEP drawing of GDC-0032 Form A—mono-methanolate solvate. Atoms are represented by 50% probability anisotropic thermal ellipsoids

Unless defined otherwise, technical and scientific terms used herein have the same meaning as commonly understood by one of ordinary skill in the art to which this invention belongs, and are consistent with:

DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about +−0.0.2 degrees 2-theta (θ). A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

"Polymorph", as used herein, refers to the occurrence of different crystalline forms of a compound. Crystalline forms have different arrangements and/or conformations of the molecule in the crystal lattice. Solvates are crystal forms containing either stoichiometric or nonstoichiometric amounts of a solvent. If the incorporated solvent is water, the solvate is commonly known as a hydrate. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3:33 (1986); J. K. Haleblian and W. McCrone, J. Pharm. Sci., 58:911 (1969); "Polymorphism in Pharmaceutical Solids, Second Edition (Drugs and the Pharmaceutical Sciences)", Harry G. Brittain, Ed. (2011) CRC Press (2009); and J. K. Haleblian, J. Pharm. Sci., 64, 1269 (1975), all of which are incorporated herein by reference.

The acronym "XRPD" means X-ray powder diffraction, an analytical technique which measures the diffraction of X-rays in the presence of a solid component. Materials which are crystalline and have regular repeating arrays of atoms generate a distinctive powder pattern. Materials with similar unit cells will give powder patterns that are similar in position as measured in °2θ (theta). Solvates which exhibit this property are called isostructural or isomorphous solvates. The intenisty of the reflections vary according to the electron density causing diffraction as well as sample, sample preparation, and instrument parameters. Analysis of XRPD data is based upon the general appearance of the measured powder pattern(s) with respect to the known response of the X-ray diffraction system used to collect the data. For diffraction peaks that may be present in the powder pattern, their positions, shapes, widths and relative intensity distributions can be used to characterize the type of solid state order in the powder sample. The position, shape and intensity of any broad diffuse scatter (halos) on top of the instrumental background can be used to characterize the level and type of solid state disorder. The combined interpretation of the solid state order and disorder present in a powder sample provides a qualitative measure of the macrostructure of the sample.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic malignancies include non-Hodgkin's lymphoma, diffuse large hematopoietic lymphoma, follicular lymphoma, mantle cell lymphoma, chronic lymphocytic leukemia, multiple myeloma, acute myelogenous leukemia, and myeloid cell leukemia. Lymphocytic leukemia (or "lymphoblastic") includes Acute lymphoblastic leukemia (ALL) and Chronic lymphocytic leukemia (CLL). Myelogenous leukemia (also "myeloid" or "non-lymphocytic") includes Acute myelogenous (or Myeloblastic) leukemia (AML) and Chronic myelogenous leukemia (CML).

A "chemotherapeutic agent" is a biological (large molecule) or chemical (small molecule) compound useful in the treatment of cancer, regardless of mechanism of action. Chemotherapeutic agents include, but are not limited to, 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole.

The term "mammal" includes, but is not limited to, humans, mice, rats, guinea pigs, monkeys, dogs, cats, horses, cows, pigs and sheep.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Polymorphs of GDC-0032

The present invention includes polymorphs of GDC-0032, and processes, methods, and reagents for the production of polymorphs of GDC-0032, shown as Formula I (Roche RG7604, CAS Reg. No. 1282512-48-4):

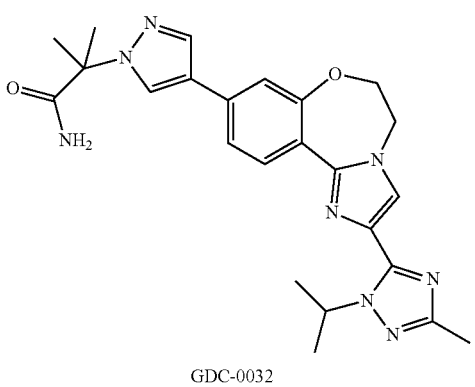

GDC-0032 and named as: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (U.S. Pat. No. 8,242,104; WO 2011/036280 which are expressly incorporated by reference). As used herein, GDC-0032 includes all stereoisomers, geometric isomers, tautomers, and pharmaceutically acceptable salts thereof.

The triclinic cell parameters and calculated volume for GDC-0032 Form B at 150K are: a=9.7944(14), b=10.4767 (11), c=12.5994(17) Å, α=96.145(10), β=95.749(11), β=115.072(9)°, V=1149.0(3) Å$^3$. The formula weight of the asymmetric unit in the crystal structure of GDC-0032 Form B is 460.541 amu·(formula unit)$^{-1}$ with Z=2, resulting in a calculated density of 1.33 g cm$^{-3}$. The space group was determined to be P-1 (no. 2). A summary of the crystal data and crystallographic data collection parameters are provided in Table 8 of Example 13.

The quality of the structure obtained is moderate, as indicated by the R-value of 0.060 (6.0%). Usually R-values in the range of 0.02 to 0.05 are quoted for the most reliably determined structures (Glusker, Jenny Pickworth; Trueblood, Kenneth N. *Crystal Structure Analysis: A Primer*, 2$^{nd}$ ed.; Oxford University press: New York, (1985), p. 87).

Figure 3:
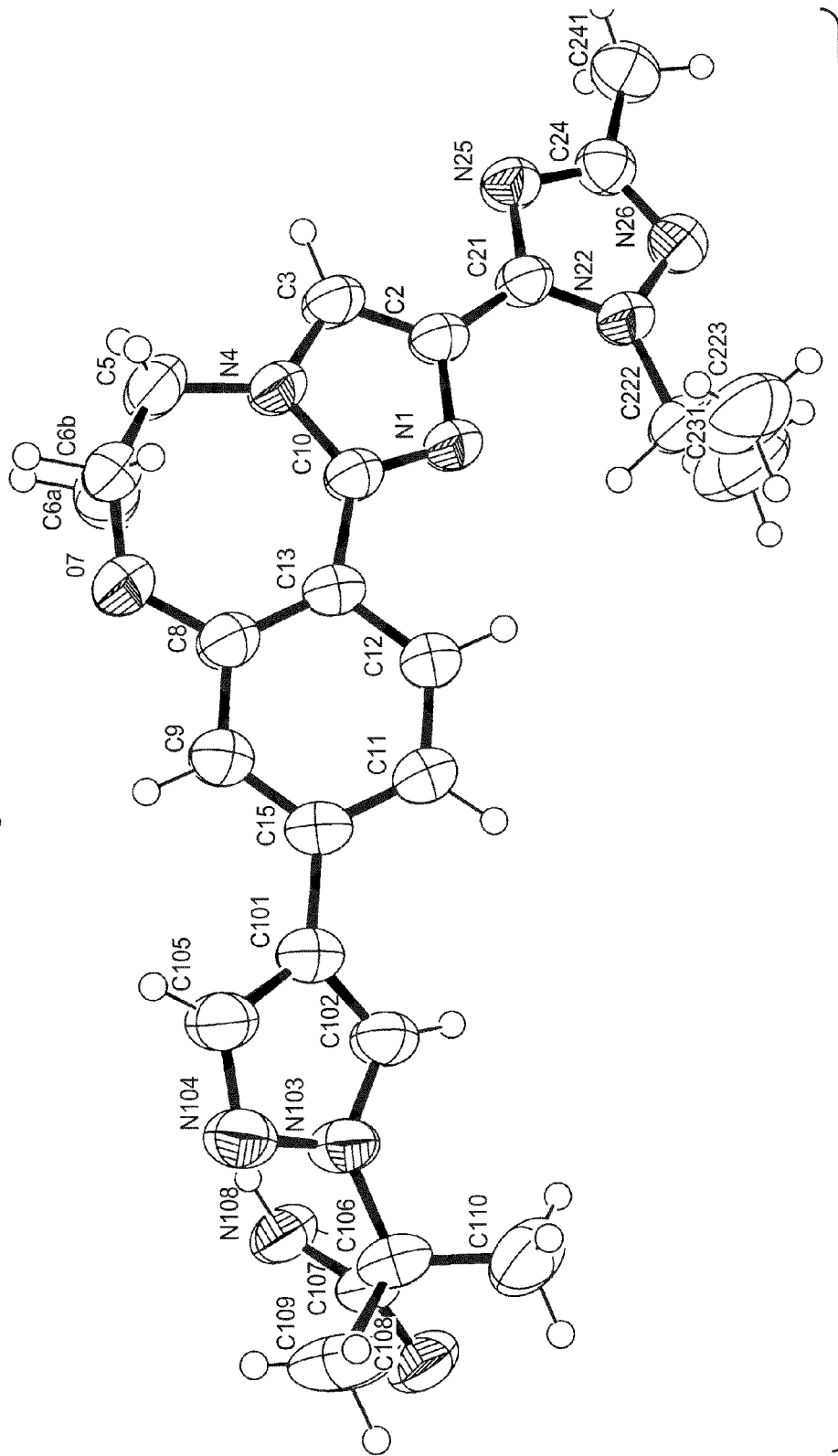
FIG. 3 shows ORTEP drawing of GDC-0032 Form B—non-solvate. Atoms are represented by 50% probability anisotropic thermal ellipsoids.

An ORTEP drawing of GDC-0032 is shown in FIG. 3. There is conformational disorder at C6 with the carbon partially occupying two different positions (31.3% for C6A and 68.7% % for C6B). The molecule observed in the asymmetric unit of the single crystal structure is consistent with the Formula I molecular structure. The asymmetric unit shown in 3 contains one GDC-0032 molecule.

Figure 7:
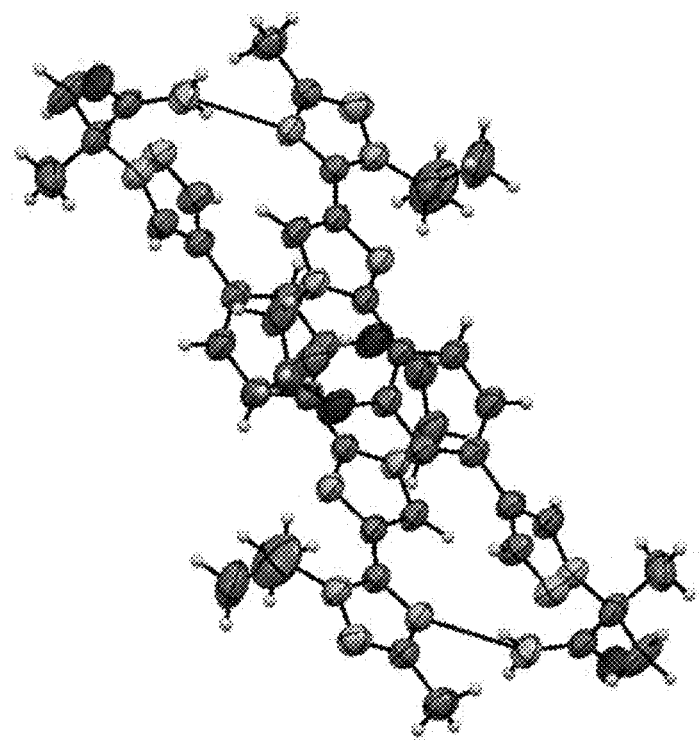
FIG. 7 shows Hydrogen bonding in GDC-0032 as viewed down the crystallographic c axis.
Figure 8:
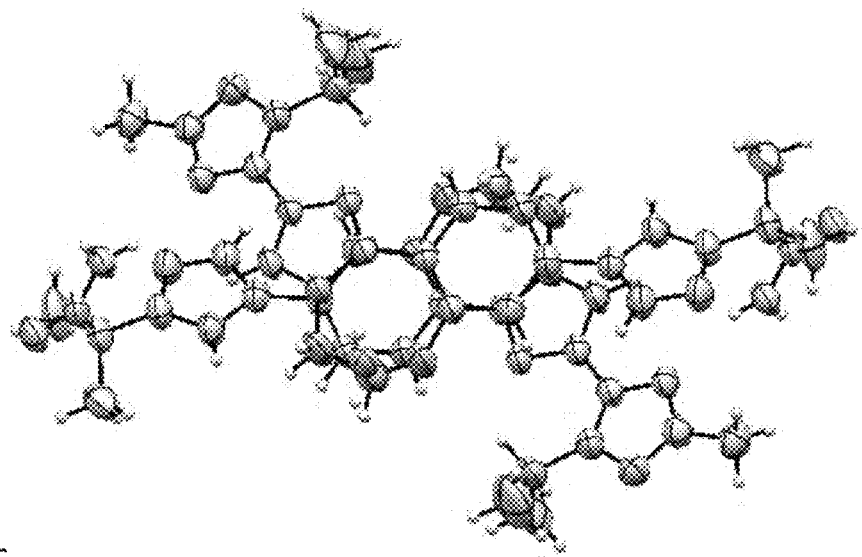
FIG. 8 shows Apparent π-Stacking Interaction in GDC-0032.

Packing diagrams viewed along the a, b, and c crystallographic axes are shown in FIGS. 4, 5, and 6 respectively. There are no solvent accessible voids. Hydrogen bonding is viewed in FIG. 7. The hydrogen bonding forms a head to tail dimer with the amide N108 acting as the hydrogen donor and triazine N25 acting as the acceptor (numbering scheme from FIG. 3). The donor acceptor distance is 2.965 (5) Å and the donor-hydrogen-acceptor bond angle is 153 (3)°. There is also an apparent intermolecular π-stacking (pi-stacking) interaction in the GDC-0032 dimer between the benzene ring of one molecule and the imidazole ring of a second molecule (FIG. 8).

Figure 9:
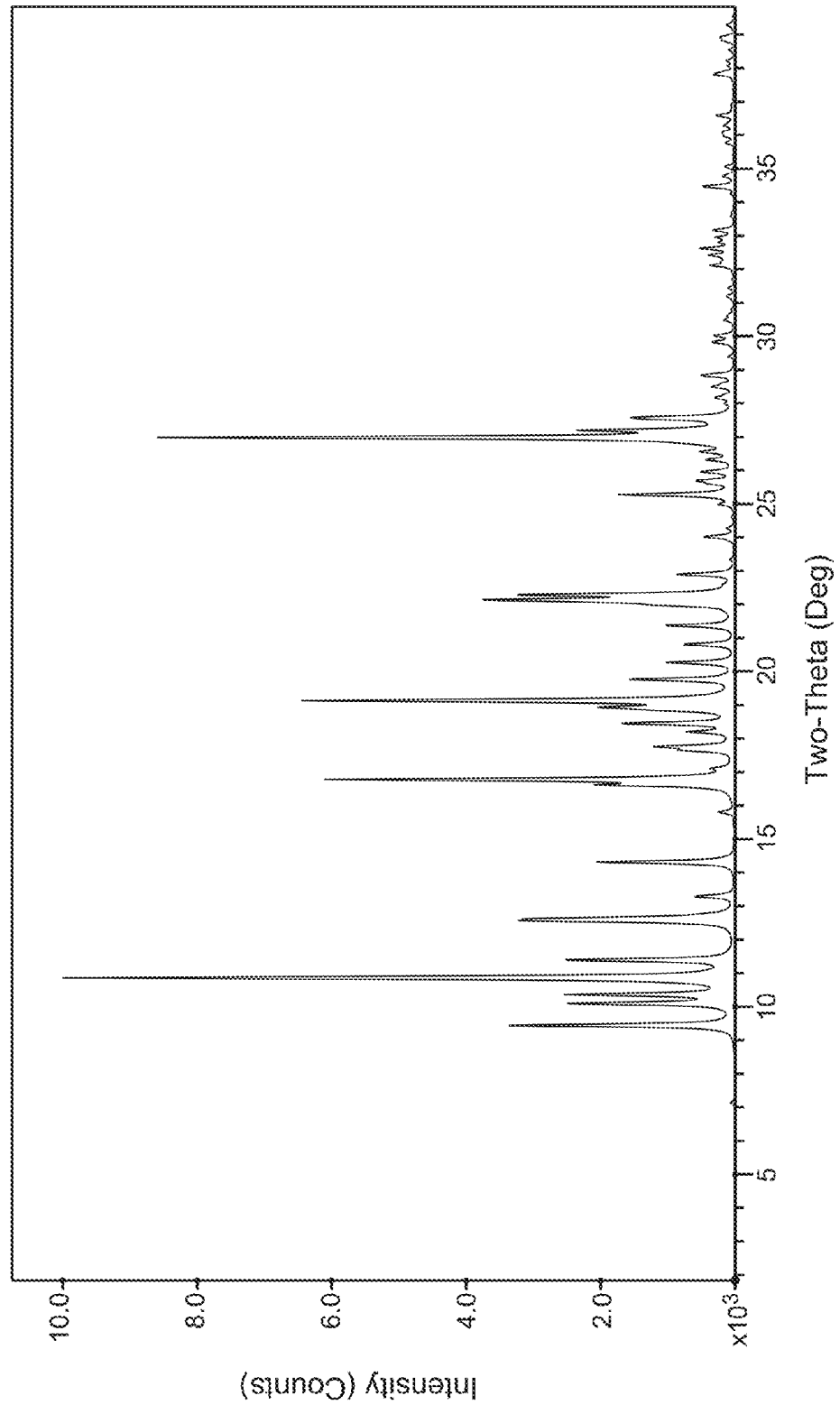
FIG. 9 shows Calculated X-ray powder pattern of GDC-0032.
Figure 10:
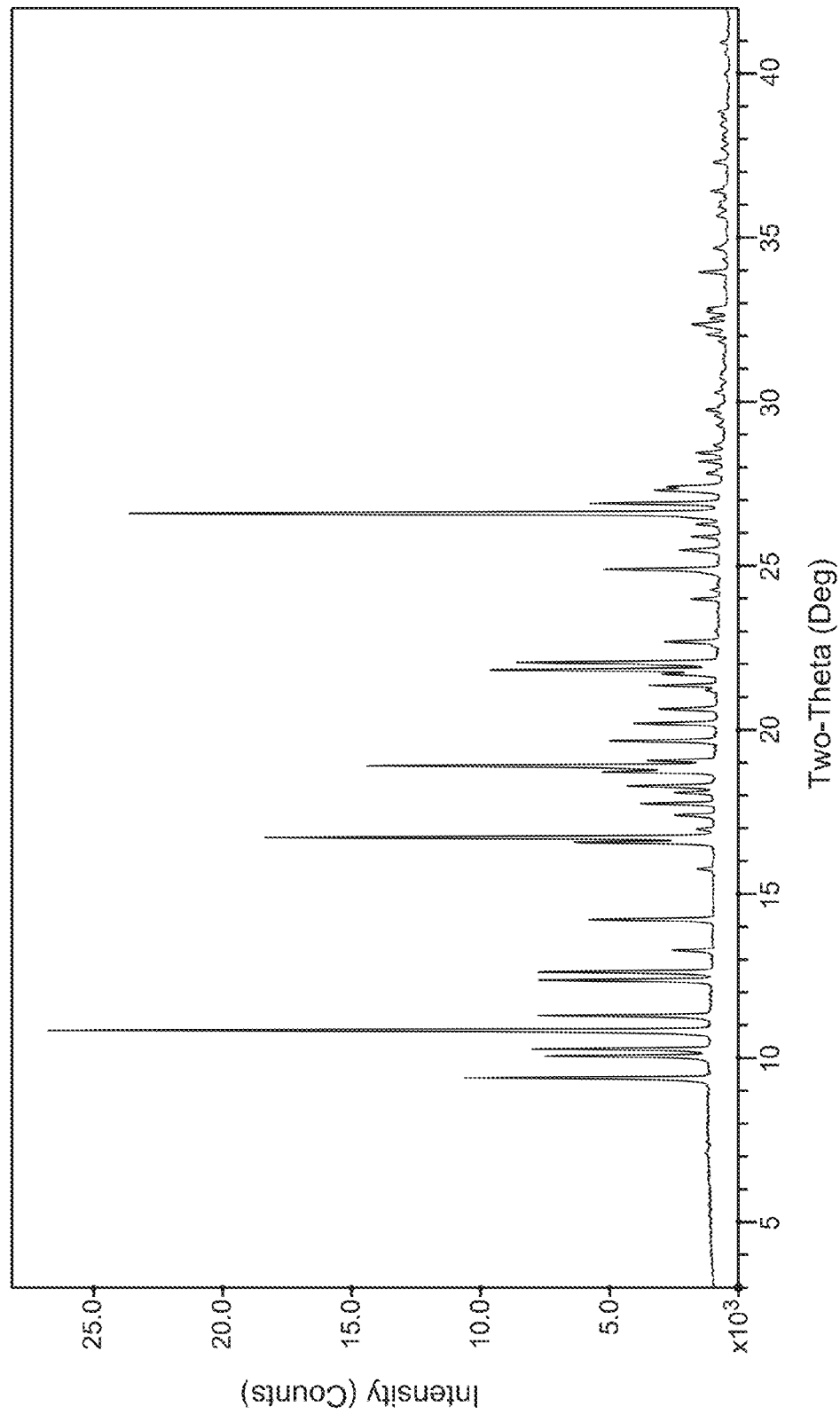
FIG. 10 shows XRPD Data of GDC-0032 Form B.

FIG. 9 shows a calculated XRPD pattern of GDC-0032 Form B generated from the single crystal data. The experimental XRPD pattern of GDC-0032 Form B is shown in FIG. 10. The calculated powder pattern from the single crystal data and the experimental pattern were obtained at 150° C. and approximately 295° C., respectively. Due to the temperature differences, anisotropic expansion or contraction of the unit cell parameters, a, b, c and angles α, β, γ may occur causing shifting of the reflections in the two patterns relative to one another. All the reflections in the experimental pattern are represented in the calculated pattern, indicating that the bulk material is likely a single phase and that it is the same phase as the single crystal.

Form B polymorph positional parameters and their estimated standard deviations (Table 1), anisotropic temperature factor coefficients (Table 2), bond distances (Table 3), bond angles (Table 4), hydrogen bonds and angles (Table 5) and torsion angles (Table 6) are shown below.

TABLE 1

Positional Parameters and Their Estimated Standard Deviations for GDC-0032

| Atom | x | y | z | U(Å$^2$) |
|---|---|---|---|---|
| O7 | 0.7024(3) | 0.7667(2) | 0.41140(17) | 0.0891(8) |
| O107 | 1.1887(2) | 0.6160(2) | 1.08382(14) | 0.0737(8) |
| N1 | 0.4169(2) | 0.30869(19) | 0.31813(14) | 0.0508(7) |
| N4 | 0.4357(2) | 0.51095(19) | 0.27035(15) | 0.0542(7) |
| N22 | 0.1519(2) | 0.0206(2) | 0.24411(16) | 0.0582(7) |
| N23 | 0.0149(2) | −0.0888(2) | 0.19615(17) | 0.0647(8) |
| N25 | 0.0383(2) | 0.1160(2) | 0.14412(15) | 0.0542(7) |
| N103 | 1.1834(2) | 0.6862(2) | 0.81079(15) | 0.0577(7) |
| N104 | 1.2508(2) | 0.8142(2) | 0.77766(16) | 0.0643(8) |
| N108 | 1.0902(3) | 0.7417(3) | 0.9983(2) | 0.0649(9) |
| C2 | 0.2915(2) | 0.2825(2) | 0.24398(17) | 0.0483(7) |
| C3 | 0.3022(3) | 0.4056(2) | 0.21343(19) | 0.0556(8) |
| C5 | 0.4831(4) | 0.6616(3) | 0.2687(3) | 0.0820(11) |
| C8 | 0.7329(3) | 0.6613(3) | 0.44724(19) | 0.0560(8) |
| C9 | 0.8576(3) | 0.7088(3) | 0.52835(19) | 0.0602(9) |
| C10 | 0.9019(3) | 0.6174(3) | 0.57593(17) | 0.0531(8) |
| C11 | 0.8179(3) | 0.4731(3) | 0.5377(2) | 0.0642(9) |
| C12 | 0.6938(3) | 0.4251(3) | 0.4580(2) | 0.0620(9) |
| C13 | 0.6444(2) | 0.5158(2) | 0.41105(17) | 0.0496(8) |
| C14 | 0.5014(2) | 0.4474(2) | 0.33361(17) | 0.0484(8) |
| C21 | 0.1639(2) | 0.1420(2) | 0.21120(17) | 0.0489(8) |
| C24 | −0.0481(3) | −0.0253(3) | 0.13802(19) | 0.0562(9) |
| C6A | 0.5737(15) | 0.7493(11) | 0.3616(14) | 0.076(4) |
| C6B | 0.6436(8) | 0.7536(4) | 0.3075(5) | 0.0656(17) |
| C101 | 1.0309(3) | 0.6696(3) | 0.66476(18) | 0.0542(8) |
| C102 | 1.0522(3) | 0.5993(3) | 0.74523(19) | 0.0586(8) |
| C105 | 1.1579(3) | 0.8020(3) | 0.68971(19) | 0.0627(9) |
| C106 | 1.2509(3) | 0.6563(3) | 0.9095(2) | 0.0625(10) |
| C107 | 1.1696(3) | 0.6683(3) | 1.00426(18) | 0.0565(8) |
| C109 | 1.4176(3) | 0.7654(4) | 0.9414(3) | 0.0954(15) |
| C110 | 1.2387(4) | 0.5065(4) | 0.8879(3) | 0.0870(16) |
| C221 | 0.1691(6) | −0.1106(5) | 0.3898(4) | 0.137(2) |
| C222 | 0.2569(3) | −0.0047(3) | 0.3217(2) | 0.0717(11) |
| C223 | 0.3589(5) | −0.0450(5) | 0.2628(3) | 0.115(2) |
| C241 | −0.2040(3) | −0.1027(3) | 0.0734(2) | 0.0695(10) |
| H181 | 1.068(3) | 0.772(3) | 0.943(2) | 0.064(8)* |
| H182 | 1.049(4) | 0.754(4) | 1.056(3) | 0.108(13)* |

Starred atoms were refined isotropically
$U_{eq} = (\frac{1}{3})\Sigma_i\Sigma_j U_{ij}a^*_i a^*_j \cdot a_i \cdot a_j$

TABLE 2

Anisotropic Temperature Factor Coefficients - U's for GDC-0032

| Name | U(1, 1) | U(2, 2) | U(3, 3) | U(1, 2) | U(1, 3) | U(2, 3) |
|---|---|---|---|---|---|---|
| O7 | 0.0980(15) | 0.0574(10) | 0.0962(14) | 0.0304(10) | −0.0364(12) | 0.0128(9) |
| O107 | 0.0893(13) | 0.0883(13) | 0.0585(10) | 0.0534(11) | −0.0008(9) | 0.0224(9) |

TABLE 2-continued

Anisotropic Temperature Factor Coefficients - U's for GDC-0032

| Name | U(1, 1) | U(2, 2) | U(3, 3) | U(1, 2) | U(1, 3) | U(2, 3) |
|---|---|---|---|---|---|---|
| N1 | 0.0483(10) | 0.0536(10) | 0.0500(10) | 0.0240(9) | −0.0029(8) | 0.0100(8) |
| N4 | 0.0523(11) | 0.0524(10) | 0.0569(11) | 0.0234(9) | −0.0044(8) | 0.0150(8) |
| N22 | 0.0576(12) | 0.0537(11) | 0.0586(11) | 0.0240(9) | −0.0077(9) | 0.0082(8) |
| N23 | 0.0633(13) | 0.0528(11) | 0.0672(12) | 0.0194(10) | −0.0044(10) | 0.0067(9) |
| N25 | 0.0452(10) | 0.0576(11) | 0.0573(11) | 0.0225(9) | −0.0025(8) | 0.0099(8) |
| N103 | 0.0472(10) | 0.0680(12) | 0.0529(11) | 0.0225(9) | −0.0036(8) | 0.0121(9) |
| N104 | 0.0547(12) | 0.0662(13) | 0.0590(12) | 0.0171(10) | −0.0041(9) | 0.0106(9) |
| N108 | 0.0719(15) | 0.0771(14) | 0.0573(13) | 0.0438(12) | 0.0015(11) | 0.0183(11) |
| C2 | 0.0447(11) | 0.0568(12) | 0.0454(11) | 0.0254(10) | 0.0010(9) | 0.0085(9) |
| C3 | 0.0484(12) | 0.0618(13) | 0.0562(13) | 0.0258(11) | −0.0058(10) | 0.0143(10) |
| C5 | 0.0757(18) | 0.0572(15) | 0.100(2) | 0.0209(14) | −0.0220(16) | 0.0287(14) |
| C8 | 0.0535(13) | 0.0580(13) | 0.0566(13) | 0.0254(11) | −0.0002(10) | 0.0142(10) |
| C9 | 0.0562(14) | 0.0558(13) | 0.0589(14) | 0.0189(11) | −0.0058(11) | 0.0083(10) |
| C10 | 0.0473(12) | 0.0630(13) | 0.0462(11) | 0.0233(11) | 0.0000(9) | 0.0083(10) |
| C11 | 0.0641(15) | 0.0619(14) | 0.0653(15) | 0.0313(12) | −0.0117(12) | 0.0097(11) |
| C12 | 0.0613(15) | 0.0546(13) | 0.0647(14) | 0.0268(12) | −0.0128(11) | 0.0040(11) |
| C13 | 0.0460(12) | 0.0578(12) | 0.0447(11) | 0.0242(10) | −0.0003(9) | 0.0084(9) |
| C14 | 0.0473(12) | 0.0549(12) | 0.0466(11) | 0.0265(10) | 0.0025(9) | 0.0103(9) |
| C21 | 0.0479(12) | 0.0542(12) | 0.0465(11) | 0.0251(10) | 0.0018(9) | 0.0098(9) |
| C24 | 0.0510(13) | 0.0597(14) | 0.0552(13) | 0.0239(11) | 0.0028(10) | 0.0051(10) |
| C6A | 0.065(7) | 0.064(5) | 0.094(9) | 0.030(5) | −0.006(6) | 0.009(5) |
| C6B | 0.075(3) | 0.050(2) | 0.063(3) | 0.022(2) | −0.009(2) | 0.0162(17) |
| C101 | 0.0486(12) | 0.0620(13) | 0.0487(12) | 0.0239(11) | −0.0007(9) | 0.0059(10) |
| C102 | 0.0466(12) | 0.0621(14) | 0.0595(13) | 0.0195(11) | −0.0054(10) | 0.0105(11) |
| C105 | 0.0583(14) | 0.0671(15) | 0.0542(13) | 0.0213(12) | −0.0029(11) | 0.0134(11) |
| C106 | 0.0512(13) | 0.0807(17) | 0.0585(14) | 0.0338(13) | −0.0041(11) | 0.0146(12) |
| C107 | 0.0525(13) | 0.0615(13) | 0.0521(12) | 0.0255(11) | −0.0087(10) | 0.0093(10) |
| C109 | 0.0487(15) | 0.136(3) | 0.085(2) | 0.0260(17) | −0.0121(14) | 0.036(2) |
| C110 | 0.112(3) | 0.106(2) | 0.0761(19) | 0.079(2) | 0.0115(18) | 0.0190(16) |
| C221 | 0.147(4) | 0.145(4) | 0.124(3) | 0.059(3) | 0.004(3) | 0.082(3) |
| C222 | 0.0754(18) | 0.0585(14) | 0.0771(17) | 0.0307(13) | −0.0162(14) | 0.0158(12) |
| C223 | 0.093(3) | 0.142(3) | 0.132(3) | 0.075(3) | −0.006(2) | 0.032(3) |
| C241 | 0.0513(14) | 0.0711(16) | 0.0720(16) | 0.0178(12) | −0.0009(12) | 0.0035(13) |

The form of the anisotropic temperature factor is: $\exp[-2\pi^2 h^2 a^{*2} U(1, 1) + k^2 b^{*2} U(2, 2) + l^2 c^{*2} U(3, 3) + 2hka^*b^*U(1, 2) + 2hla^*c^*U(1, 3) + 2klb^*c^*U(2, 3)]$ where $a^*$, $b^*$, and $c^*$ are reciprocal lattice constants.

TABLE 3

Bond Distances in Angstroms for GDC-0032

| Atom 1 | Atom 2 | Distance | Atom 1 | Atom 2 | Distance |
|---|---|---|---|---|---|
| O7 | C6A | 1.280(10) | C11 | C12 | 1.367(3) |
| O7 | C6B | 1.345(5) | C11 | H11 | 0.950 |
| O7 | C8 | 1.369(3) | C12 | C13 | 1.393(3) |
| O107 | C107 | 1.227(3) | C12 | H12 | 0.950 |
| N1 | C14 | 1.312(3) | C13 | C14 | 1.467(3) |
| N1 | C2 | 1.373(3) | C24 | C241 | 1.487(3) |
| N4 | C3 | 1.364(3) | C6A | H6A1 | 0.990 |
| N4 | C14 | 1.367(3) | C6A | H6A2 | 0.990 |
| N4 | C5 | 1.447(3) | C6B | H6B1 | 0.990 |
| N22 | C21 | 1.342(3) | C6B | H6B2 | 0.990 |
| N22 | N23 | 1.366(3) | C101 | C102 | 1.365(3) |
| N22 | C222 | 1.473(3) | C101 | C105 | 1.391(3) |
| N23 | C24 | 1.313(3) | C102 | H102 | 0.950 |
| N25 | C21 | 1.327(3) | C105 | H105 | 0.950 |
| N25 | C24 | 1.347(3) | C106 | C110 | 1.515(4) |
| N103 | C102 | 1.341(3) | C106 | C107 | 1.523(4) |
| N103 | N104 | 1.354(3) | C106 | C109 | 1.524(4) |
| N103 | C106 | 1.476(3) | C109 | H10A | 0.980 |
| N104 | C105 | 1.320(3) | C109 | H10B | 0.980 |
| N108 | C107 | 1.307(3) | C109 | H10C | 0.980 |
| N108 | H181 | 0.84(3) | C110 | H11A | 0.980 |
| N108 | H182 | 0.89(4) | C110 | H11B | 0.980 |
| C2 | C3 | 1.350(3) | C110 | H11C | 0.980 |
| C2 | C21 | 1.451(3) | C221 | C222 | 1.500(5) |
| C3 | H3 | 0.950 | C221 | H22A | 0.980 |
| C5 | C6A | 1.369(12) | C221 | H22B | 0.980 |
| C5 | C6B | 1.449(6) | C221 | H22C | 0.980 |
| C5 | H5A | 0.990 | C222 | C223 | 1.471(5) |
| C5 | H5B | 0.990 | C222 | H222 | 1.000 |
| C8 | C9 | 1.382(3) | C223 | H22D | 0.980 |
| C8 | C13 | 1.391(3) | C223 | H22E | 0.980 |
| C9 | C10 | 1.374(3) | C223 | H22F | 0.980 |
| C9 | H9 | 0.950 | C241 | H24A | 0.980 |
| C10 | C11 | 1.380(3) | C241 | H24B | 0.980 |
| C10 | C101 | 1.466(3) | C241 | H24C | 0.980 |

Numbers in parentheses are standard uncertainties in the least significant digits.

TABLE 4

Bond Angles in Degrees for GDC-0032

| Atom 1 | Atom 2 | Atom 3 | Angle | Atom 1 | Atom 2 | Atom 3 | Angle |
|---|---|---|---|---|---|---|---|
| C6A | O7 | C6B | 44.9(7) | C11 | C12 | H12 | 118.50 |
| C6A | O7 | C8 | 125.4(5) | C13 | C12 | H12 | 118.50 |
| C6B | O7 | C8 | 121.0(3) | C8 | C13 | C12 | 115.9(2) |

TABLE 4-continued

Bond Angles in Degrees for GDC-0032

| Atom 1 | Atom 2 | Atom 3 | Angle | Atom 1 | Atom 2 | Atom 3 | Angle |
|---|---|---|---|---|---|---|---|
| C14 | N1 | C2 | 105.89(18) | C8 | C13 | C14 | 127.5(2) |
| C3 | N4 | C14 | 107.24(18) | C12 | C13 | C14 | 116.6(2) |
| C3 | N4 | C5 | 123.60(19) | N1 | C14 | N4 | 110.58(18) |
| C14 | N4 | C5 | 128.85(19) | N1 | C14 | C13 | 121.40(19) |
| C21 | N22 | N23 | 109.21(18) | N4 | C14 | C13 | 128.0(2) |
| C21 | N22 | C222 | 130.2(2) | N25 | C21 | N22 | 109.60(19) |
| N23 | N22 | C222 | 120.50(19) | N25 | C21 | C2 | 124.0(2) |
| C24 | N23 | N22 | 102.99(19) | N22 | C21 | C2 | 126.4(2) |
| C21 | N25 | C24 | 103.72(19) | N23 | C24 | N25 | 114.5(2) |
| C102 | N103 | N104 | 111.37(19) | N23 | C24 | C241 | 122.5(2) |
| C102 | N103 | C106 | 127.3(2) | N25 | C24 | C241 | 123.0(2) |
| N104 | N103 | C106 | 121.30(19) | O7 | C6A | C5 | 132.0(13) |
| C105 | N104 | N103 | 103.98(19) | O7 | C6A | H6A1 | 104.20 |
| C107 | N108 | H181 | 125.8(19) | C5 | C6A | H6A1 | 104.20 |
| C107 | N108 | H182 | 117(2) | O7 | C6A | H6A2 | 104.20 |
| H181 | N108 | H182 | 117(3) | C5 | C6A | H6A2 | 104.20 |
| C3 | C2 | N1 | 110.21(19) | H6A1 | C6A | H6A2 | 105.50 |
| C3 | C2 | C21 | 126.6(2) | O7 | C6B | C5 | 120.0(5) |
| N1 | C2 | C21 | 123.07(19) | O7 | C6B | H6B1 | 107.30 |
| C2 | C3 | N4 | 106.07(19) | C5 | C6B | H6B1 | 107.30 |
| C2 | C3 | H3 | 127.00 | O7 | C6B | H6B2 | 107.30 |
| N4 | C3 | H3 | 127.00 | C5 | C6B | H6B2 | 107.30 |
| C6A | C5 | N4 | 114.3(5) | H6B1 | C6B | H6B2 | 106.90 |
| C6A | C5 | C6B | 41.7(6) | C102 | C101 | C105 | 103.3(2) |
| N4 | C5 | C6B | 115.4(3) | C102 | C101 | C10 | 127.5(2) |
| C6A | C5 | H5A | 108.70 | C105 | C101 | C10 | 129.2(2) |
| N4 | C5 | H5A | 108.70 | N103 | C102 | C101 | 108.3(2) |
| C6B | C5 | H5A | 69.40 | N103 | C102 | H102 | 125.90 |
| C6A | C5 | H5B | 108.70 | C101 | C102 | H102 | 125.90 |
| N4 | C5 | H5B | 108.70 | N104 | C105 | C101 | 113.1(2) |
| C6B | C5 | H5B | 134.30 | N104 | C105 | H105 | 123.50 |
| H5A | C5 | H5B | 107.60 | C101 | C105 | H105 | 123.50 |
| O7 | C8 | C9 | 114.9(2) | N103 | C106 | C110 | 109.1(2) |
| O7 | C8 | C13 | 124.5(2) | N103 | C106 | C107 | 111.43(19) |
| C9 | C8 | C13 | 120.5(2) | C110 | C106 | C107 | 109.1(2) |
| C10 | C9 | C8 | 122.7(2) | N103 | C106 | C109 | 109.4(2) |
| C10 | C9 | H9 | 118.70 | C110 | C106 | C109 | 110.4(3) |
| C8 | C9 | H9 | 118.70 | C107 | C106 | C109 | 107.4(2) |
| C9 | C10 | C11 | 117.1(2) | O107 | C107 | N108 | 123.7(3) |
| C9 | C10 | C101 | 121.8(2) | O107 | C107 | C106 | 118.7(2) |
| C11 | C10 | C101 | 121.1(2) | N108 | C107 | C106 | 117.5(2) |
| C12 | C11 | C10 | 120.7(2) | C106 | C109 | H10A | 109.50 |
| C12 | C11 | H11 | 119.70 | C106 | C109 | H10B | 109.50 |
| C10 | C11 | H11 | 119.70 | H10A | C109 | H10B | 109.50 |
| C11 | C12 | C13 | 123.1(2) | C106 | C109 | H10C | 109.50 |
| H10A | C109 | H10C | 109.50 | N22 | C222 | C221 | 110.4(3) |
| H10B | C109 | H10C | 109.50 | C223 | C222 | H222 | 107.50 |
| C106 | C110 | H11A | 109.50 | N22 | C222 | H222 | 107.50 |
| C106 | C110 | H11B | 109.50 | C221 | C222 | H222 | 107.50 |
| H11A | C110 | H11B | 109.50 | C222 | C223 | H22D | 109.50 |
| C106 | C110 | H11C | 109.50 | C222 | C223 | H22E | 109.50 |
| H11A | C110 | H11C | 109.50 | H22D | C223 | H22E | 109.50 |
| H11B | C110 | H11C | 109.50 | C222 | C223 | H22F | 109.50 |
| C222 | C221 | H22A | 109.50 | H22D | C223 | H22F | 109.50 |
| C222 | C221 | H22B | 109.50 | H22E | C223 | H22F | 109.50 |
| H22A | C221 | H22B | 109.50 | C24 | C241 | H24A | 109.50 |
| C222 | C221 | H22C | 109.50 | C24 | C241 | H24B | 109.50 |
| H22A | C221 | H22C | 109.50 | H24A | C241 | H24B | 109.50 |
| H22B | C221 | H22C | 109.50 | C24 | C241 | H24C | 109.50 |
| C223 | C222 | N22 | 109.2(2) | H24A | C241 | H24C | 109.50 |
| C223 | C222 | C221 | 114.4(3) | H24B | C241 | H24C | 109.50 |

Numbers in parentheses are standard uncertainties in the least significant digits.

TABLE 5

Hydrogen Bond Distances in Angstroms and Angles in Degrees for GDC-0032

| D | H | A | D-H | A-H | D-A | D-H-A |
|---|---|---|---|---|---|---|
| N108 | H181 | N25 | 0.84(3) | 2.18(3) | 2.956(5) | 153(3) |

Numbers in parentheses are standard uncertainties in the least significant digits.

TABLE 6

Torsion Angles in Degrees for GDC-0032

| Atom 1 | Atom 2 | Atom 3 | Atom 4 | Angle |
|---|---|---|---|---|
| C6A | O7 | C8 | C9 | −159.00(0.96) |
| C6A | O7 | C8 | C13 | 18.03(1.02) |
| C6B | O7 | C8 | C9 | 146.90(0.43) |
| C6B | O7 | C8 | C13 | −36.07(0.55) |

TABLE 6-continued

Torsion Angles in Degrees for GDC-0032

| Atom 1 | Atom 2 | Atom 3 | Atom 4 | Angle |
|---|---|---|---|---|
| C8 | O7 | C6A | C5 | −56.21(1.75) |
| C8 | O7 | C6A | C6B | −100.44(0.73) |
| C6B | O7 | C6A | C5 | 44.23(1.18) |
| C8 | O7 | C6B | C5 | 76.44(0.66) |
| C8 | O7 | C6B | C6A | 110.82(0.79) |
| C6A | O7 | C6B | C5 | −34.38(0.79) |
| C14 | N1 | C2 | C3 | 1.11(0.26) |
| C14 | N1 | C2 | C21 | −175.14(0.20) |
| C2 | N1 | C14 | N4 | −1.08(0.25) |
| C2 | N1 | C14 | C13 | 178.22(0.19) |
| C5 | N4 | C3 | C2 | −173.93(0.25) |
| C14 | N4 | C3 | C2 | 0.04(0.27) |
| C3 | N4 | C5 | C6A | 150.91(0.77) |
| C3 | N4 | C5 | C6B | −162.96(0.36) |
| C14 | N4 | C5 | C6A | −21.69(0.85) |
| C14 | N4 | C5 | C6B | 24.44(0.51) |
| C3 | N4 | C14 | N1 | 0.67(0.26) |
| C3 | N4 | C14 | C13 | −178.57(0.22) |
| C5 | N4 | C14 | N1 | 174.23(0.27) |
| C5 | N4 | C14 | C13 | −5.02(0.41) |
| C21 | N22 | N23 | C24 | −0.77(0.26) |
| C222 | N22 | N23 | C24 | 177.11(0.23) |
| N23 | N22 | C21 | N25 | 0.72(0.26) |
| N23 | N22 | C21 | C2 | 179.54(0.21) |
| C222 | N22 | C21 | N25 | −176.89(0.23) |
| C222 | N22 | C21 | C2 | 1.93(0.39) |
| N23 | N22 | C222 | C221 | −37.09(0.36) |
| N23 | N22 | C222 | C223 | 89.49(0.32) |
| C21 | N22 | C222 | C221 | 140.29(0.31) |
| C21 | N22 | C222 | C223 | −93.13(0.34) |
| N22 | N23 | C24 | N25 | 0.59(0.29) |
| N22 | N23 | C24 | C241 | −177.71(0.24) |
| C24 | N25 | C21 | N22 | −0.34(0.25) |
| C24 | N25 | C21 | C2 | −179.20(0.21) |
| C21 | N25 | C24 | N23 | −0.17(0.29) |
| C21 | N25 | C24 | C241 | 178.12(0.24) |
| C102 | N103 | N104 | C105 | −0.66(0.28) |
| C106 | N103 | N104 | C105 | −178.91(0.24) |
| N104 | N103 | C102 | C101 | 0.71(0.31) |
| C106 | N103 | C102 | C101 | 178.83(0.25) |
| N104 | N103 | C106 | C107 | 101.41(0.27) |
| N104 | N103 | C106 | C109 | −17.21(0.34) |
| N104 | N103 | C106 | C110 | −138.10(0.26) |
| C102 | N103 | C106 | C107 | −76.54(0.33) |
| C102 | N103 | C106 | C109 | 164.84(0.27) |
| C102 | N103 | C106 | C110 | 43.95(0.39) |
| N103 | N104 | C105 | C101 | 0.37(0.31) |
| N1 | C2 | C3 | N4 | −0.71(0.27) |
| C21 | C2 | C3 | N4 | 175.38(0.21) |
| N1 | C2 | C21 | N22 | −2.38(0.35) |
| N1 | C2 | C21 | N25 | 176.28(0.21) |
| C3 | C2 | C21 | N22 | −178.00(0.24) |
| C3 | C2 | C21 | N25 | 0.66(0.37) |
| N4 | C5 | C6A | O7 | 58.13(1.55) |
| N4 | C5 | C6A | C6B | 101.57(0.73) |
| C6B | C5 | C6A | O7 | −43.44(1.12) |
| N4 | C5 | C6B | O7 | −64.58(0.61) |
| N4 | C5 | C6B | C6A | −98.72(0.88) |
| C6A | C5 | C6B | O7 | 34.15(0.87) |
| O7 | C8 | C9 | C10 | 178.08(0.27) |
| C13 | C8 | C9 | C10 | 0.93(0.44) |
| O7 | C8 | C13 | C12 | −179.58(0.26) |
| O7 | C8 | C13 | C14 | −3.02(0.42) |
| C9 | C8 | C13 | C12 | −2.71(0.38) |
| C9 | C8 | C13 | C14 | 173.85(0.24) |
| C8 | C9 | C10 | C11 | 1.38(0.43) |
| C8 | C9 | C10 | C101 | −177.56(0.27) |
| C9 | C10 | C11 | C12 | −1.78(0.42) |
| C101 | C10 | C11 | C12 | 177.17(0.27) |
| C9 | C10 | C101 | C102 | 152.07(0.31) |
| C9 | C10 | C101 | C105 | −25.95(0.47) |
| C11 | C10 | C101 | C102 | −26.83(0.46) |
| C11 | C10 | C101 | C105 | 155.14(0.31) |
| C10 | C11 | C12 | C13 | −0.10(0.46) |
| C11 | C12 | C13 | C8 | 2.35(0.39) |
| C11 | C12 | C13 | C14 | −174.60(0.25) |
| C8 | C13 | C14 | N1 | −169.74(0.23) |
| C8 | C13 | C14 | N4 | 9.44(0.38) |
| C12 | C13 | C14 | N1 | 6.80(0.32) |
| C12 | C13 | C14 | N4 | −174.02(0.23) |
| O7 | C6A | C6B | C5 | 147.30(0.64) |
| C5 | C6A | C6B | O7 | −147.30(0.64) |
| C10 | C101 | C102 | N103 | −178.87(0.27) |
| C105 | C101 | C102 | N103 | −0.44(0.32) |
| C10 | C101 | C105 | N104 | 178.43(0.28) |
| C102 | C101 | C105 | N104 | 0.04(0.32) |
| N103 | C106 | C107 | O107 | 163.74(0.24) |
| N103 | C106 | C107 | N108 | −20.22(0.36) |
| C109 | C106 | C107 | O107 | −76.40(0.33) |
| C109 | C106 | C107 | N108 | 99.64(0.32) |
| C110 | C106 | C107 | O107 | 43.24(0.37) |
| C110 | C106 | C107 | N108 | −140.72(0.30) |

Numbers in parentheses are standard uncertainties in the least significant digits.

Physical form screening led to characterization of different crystalline phases, polymorphs, hydrates and solvates of GDC-0032. The solubility of GDC-0032 was determined in five solvents/solvent mixtures at two different temperatures (Example 2). A number of polymorph forms of GDC-0032 were characterized, including but not limited to the following:

Form A, Methanolate

Figure 2:
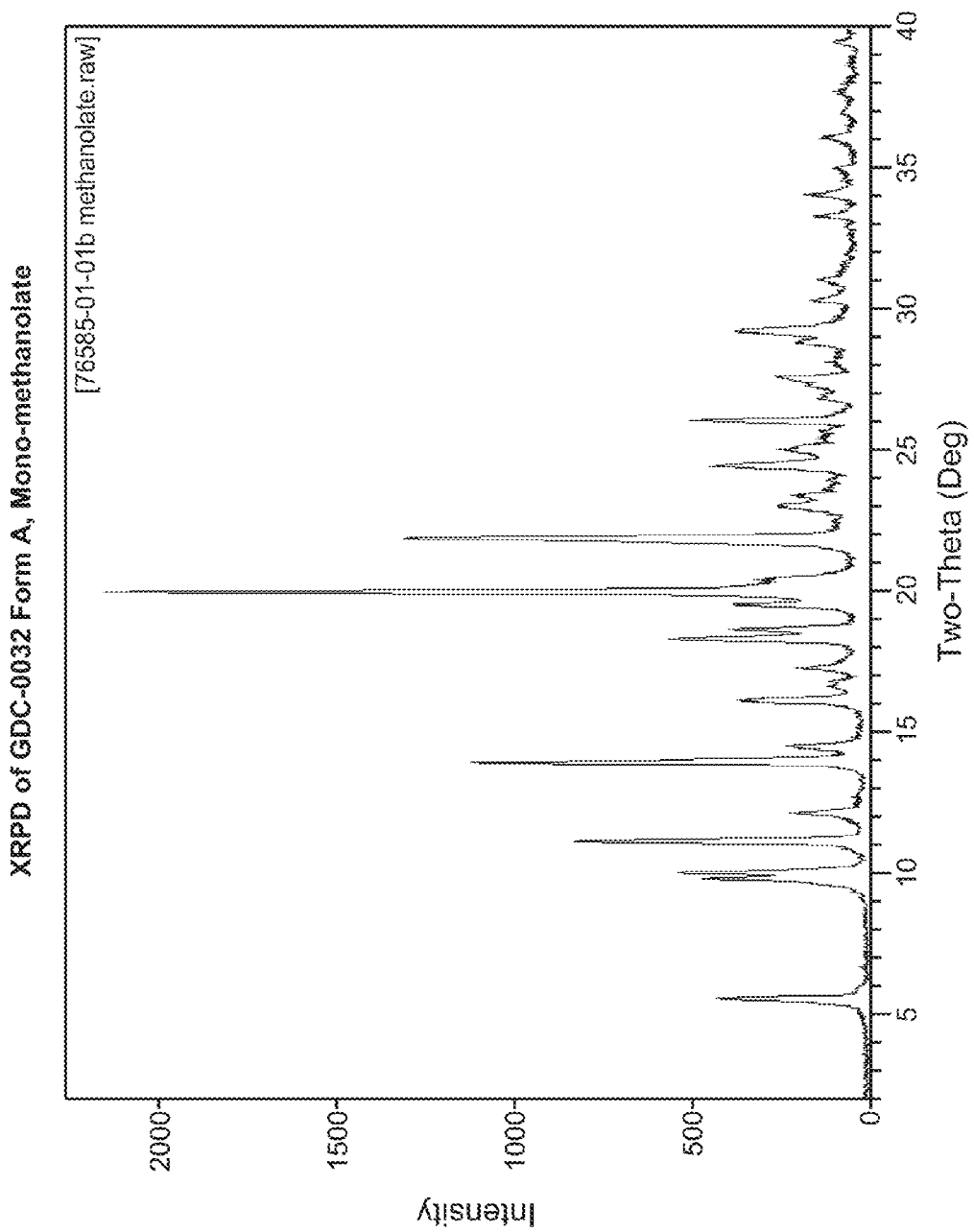
FIG. 2 shows XRPD of GDC-0032 Form A, mono-methanolate.

Form A was observed in experiments containing methanol. It was initially characterized by analysis of solids from manual experiments. Form A is a crystalline material as determined from PLM and XRPD (FIG. 2). Thermal data (TGA) collected on Form A indicated a weight loss of 6.5% by 125° C. which is consistent with the loss of one mole of methanol (theoretical weight loss for mono-methanolate: 6.5%). DSC showed an endotherm at 105-125° C. (max) consistent with weight loss in the TGA followed by an endotherm at 257° C. which is attributed to the melt as confirmed by hot-stage microscopy. Thermal desolvation of the methanolate under nitrogen or vacuum led to the formation of Form B, albeit at reduced particle size. Slurrying Form A in the presence of water at 50° C. gave Form D, the mono-hydrate. A water slurry experiment at room temperature gave a mixture of Form A and Form D after drying. It is not clear if the damp material was a mixture of forms or a mixed hydrate-methanolate solvate. In addition, a partially desolvated Form A contained 0.6 moles of methanol. Single crystal structure determination on solids crystallized from methanol confirmed the Form A is a mono-methanolate. FIG. 1 shows an ORTEP drawing of GDC-0032 Form A—mono-methanolate solvate.

Form B, Non-Solvate

Figure 11:
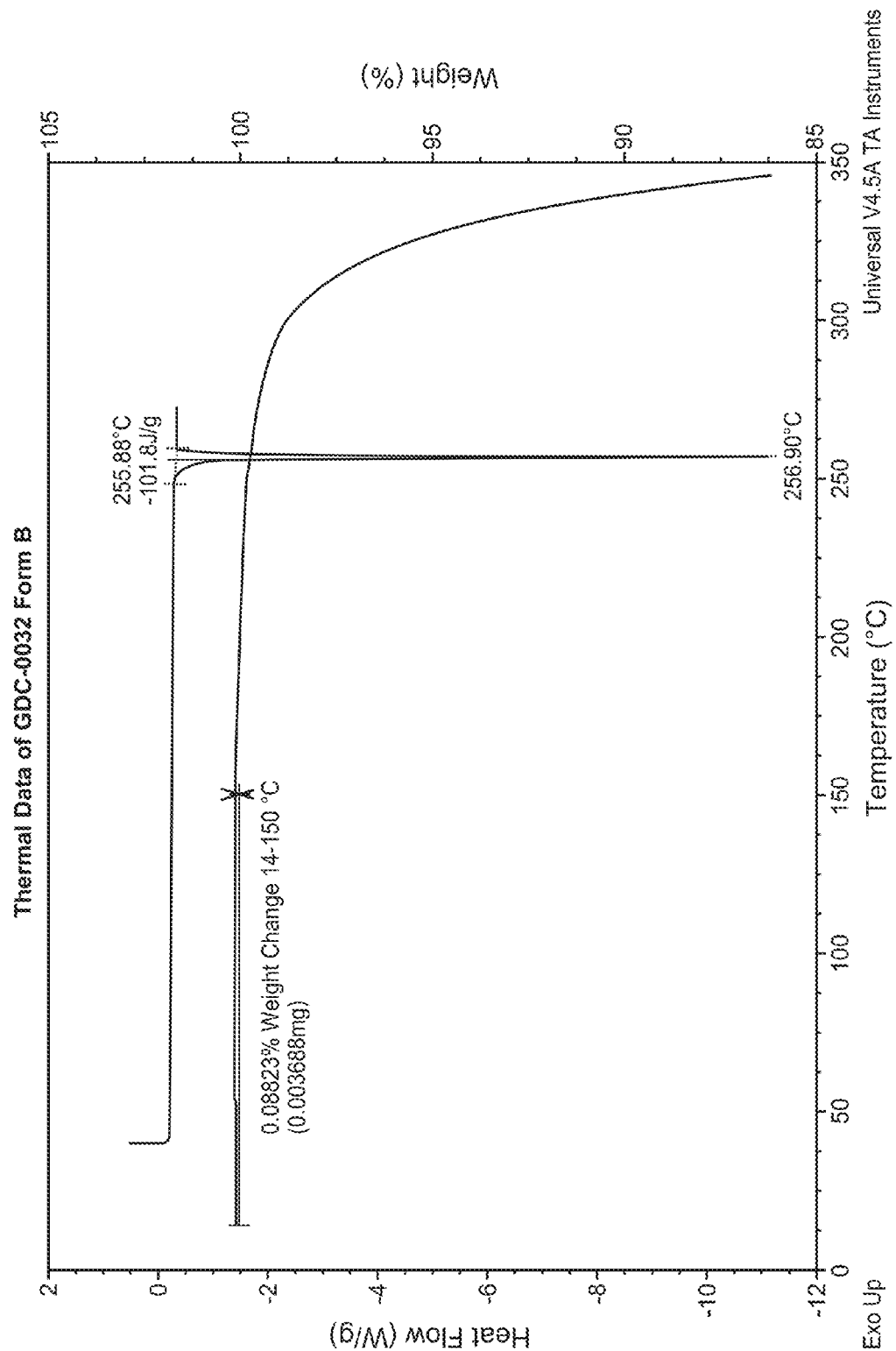
FIG. 11 shows Thermal Data of GDC-0032 Form B.
Figure 12:
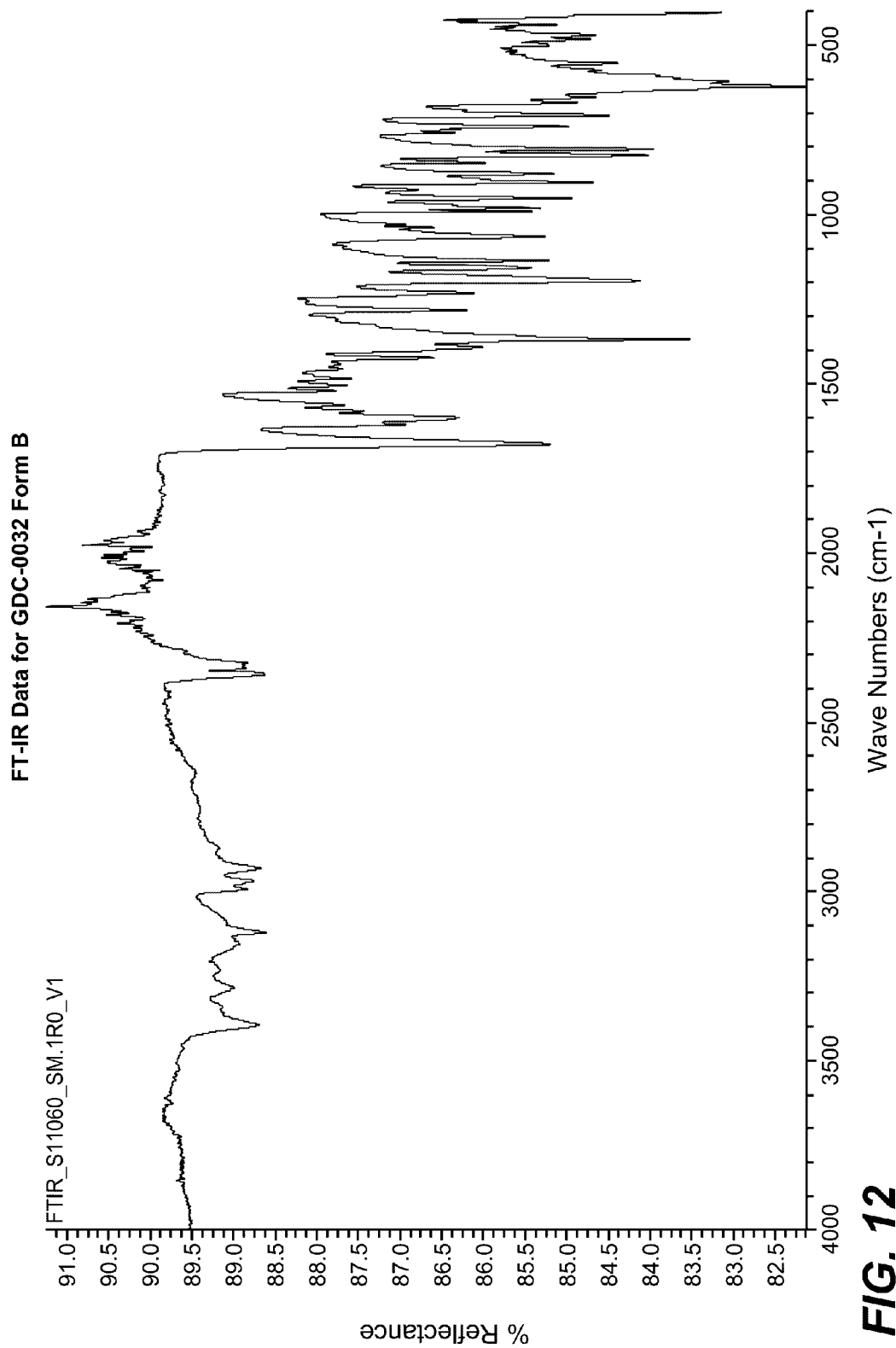
FIG. 12 shows FT-IR (Fourier transform Infrared spectroscopy) Data for GDC-0032 Form B.

Form B is a non-solvated form derived from multiple solvents and by desolvation of multiple solvates. Form B can be prepared by heating samples of the solvated forms further described in this pattern at 10° C./minute in the DSC under nitrogen. Form B is crystalline by XRPD (FIG. 10) and by PLM (Polarized Light Microscopy). FIG. 11 shows that thermal analysis (TGA) of Form B indicated little or no weight loss up to 200° C. A small weight loss, typically less than 0.5%, was observed between 200 and 270° C. probably associated with inclusion of the crystallizing solvent in the crystals. DSC analysis indicated a single endothermic event was present at 257° C. attributed to the melt. DVS data of Form B demonstrated low kinetic hygroscopicity with less than 0.3% weight gain at 95% RH. Little hysteresis was observed on the desorption cycle. The material was still Form B after the DVS experiment. Slurrying Form B in water, with and without Tween 80, gave no conversion to the hydrate. Form B was unchanged after accelerated stability tests at 40° C. and 75% RH. FIG. 12 shows the FT-IR spectrum of Form B. Single crystal structure determination confirmed that Form B is not solvated or hydrated.

Form B polymorph was selected for development based on criteria including: a propensity to form a polymorph, as opposed to a pseudo-polymorph, crystallinity, thermoanalytical data, e.g. melting point, hygroscopicity, physical stability, chemical stability in solid state, solubility, mechanical stress, powder properties, large scale manufacturability, and formulation aspects.

Form C, Mono Isoamyl Alcoholate Solvate

Figure 13:
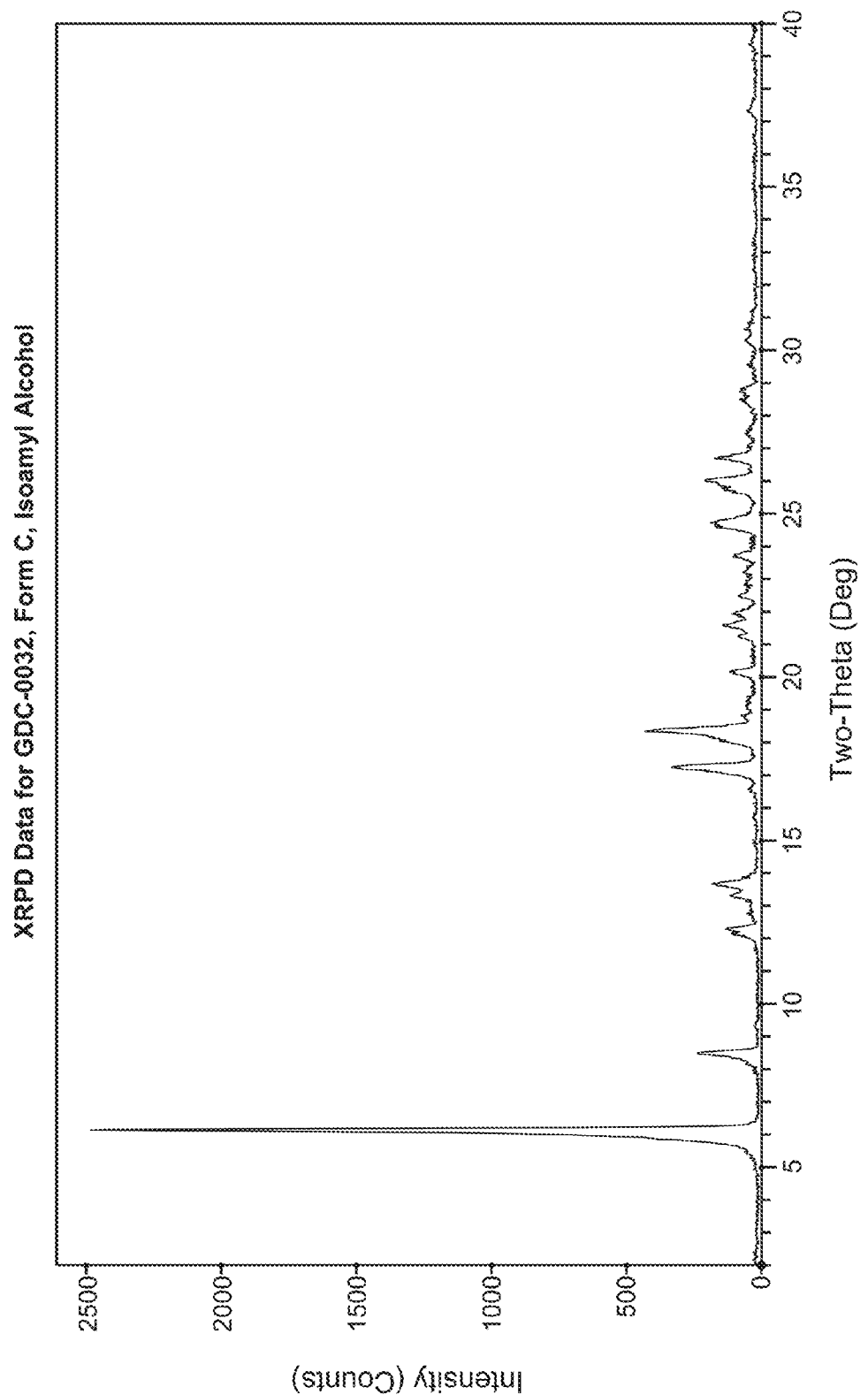
FIG. 13 shows XRPD Data for GDC-0032, Form C, isoamyl alcohol.

Form C was derived only from isoamyl alcohol and was initially formed at 5° C. It is crystalline by XRPD (FIG. 13) and PLM. It is isomorphous with Form V. TGA data on a non-dried, wet sample, shows a total weight loss of 15%. This weight loss was divided into two broad steps: a 5.2% weight loss was observed from ambient to 105° C. and an additional 9.8% weight loss was observed from 105-125° C. (bp of isoamyl alcohol: 130° C.). The theoretical weight loss for a mono-solvate is 16.1% and 8.7% for a hemi-solvate. The crystal structure of Form C was solved. Form C is the mono-isoamyl alcoholate. Desolvation of Form C under vacuum at 60° C. gave non-solvated Form B. DSC data indicate a strong, sharp endotherm at 109° C. followed by a strong endotherm, presumably the melt of Form B, at 257° C. It is not known if the endotherm at 109° C. is the incongruent melt of the solvate and/or the concurrent conversion to Form B. Slurry interconversion experiments with Form B in pure isoamyl alcohol indicated that Form B was preferred at temperature of approximately 20° C. or above. The solvate, Form C, was favored at temperatures of 15° C. or below.

Form D, Mono-Hydrate

Figure 14:
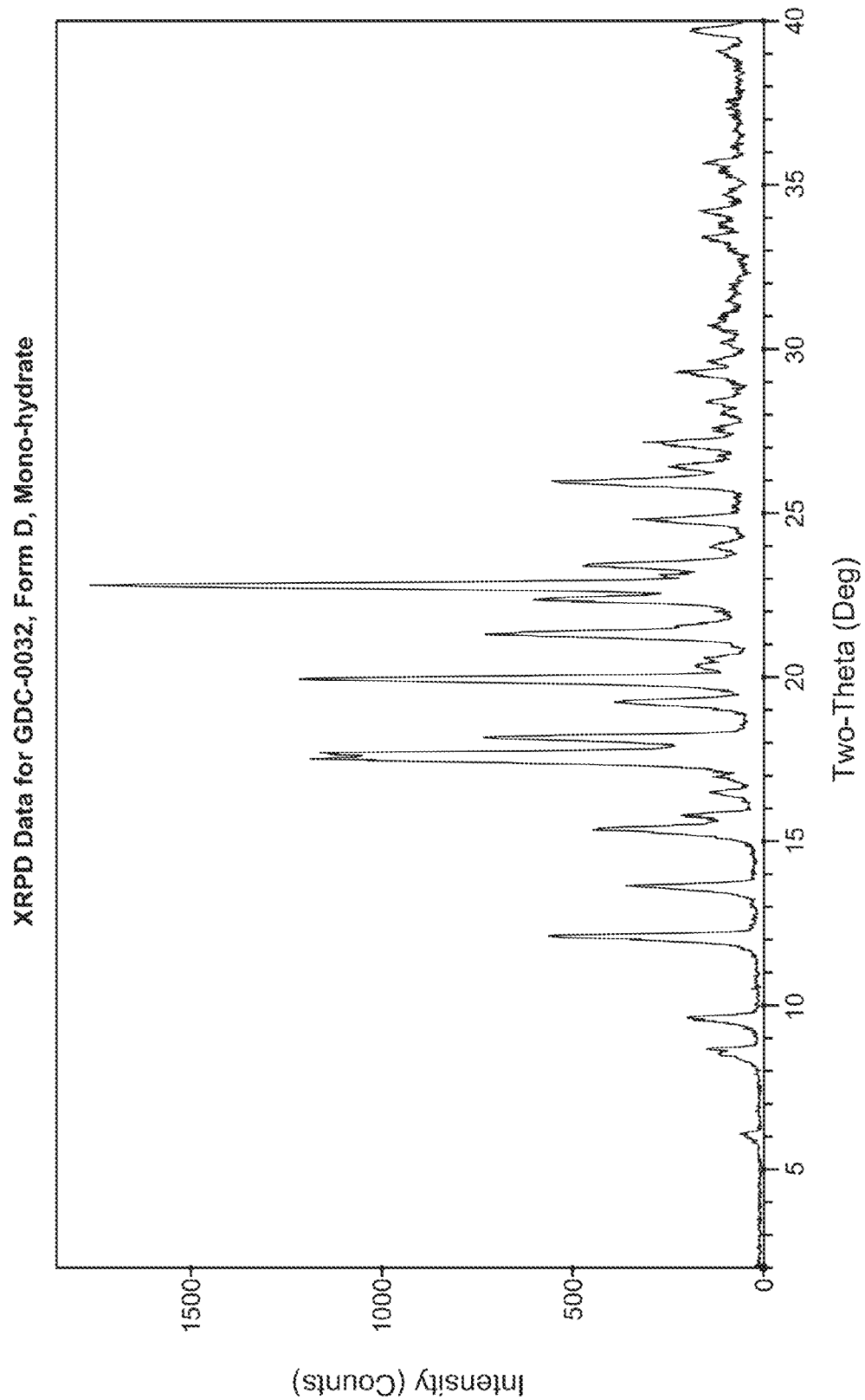
FIG. 14 shows XRPD Data for GDC-0032, Form D, mono-hydrate.

Form D is a hydrate derived from aqueous solvents at high water activity. It was not observed from Form B in the presence of pure water, water containing tween, or by gently grinding the material is the presence of water at either ambient or 60° C. Form D is crystalline by XRPD (FIG. 14) and PLM. Thermal data (TGA) indicated a weight loss of 3.7% (monohydrate theoretical 3.3%) up to 100° C. A series of isothermal TGA runs were conducted to de-risk potential wet granulation issues. Dehydration was complete on the TGA within 15 minutes at 100° C. and within 40 minutes at 60° C. DSC data indicated an endotherm at 94° C. (onset) corresponding to weight loss in the TGA. An apparent overlapping melt-recrystallization was observed at 137 and 150° C. respectively followed by melting, of Form B, at 257° C. No further work to characterize these transitions was done. Single crystal structure determination was conducted and confirms that Form D is the mono-hydrate.

Form E, Mono-Trifluoroethanolate

Figure 15:
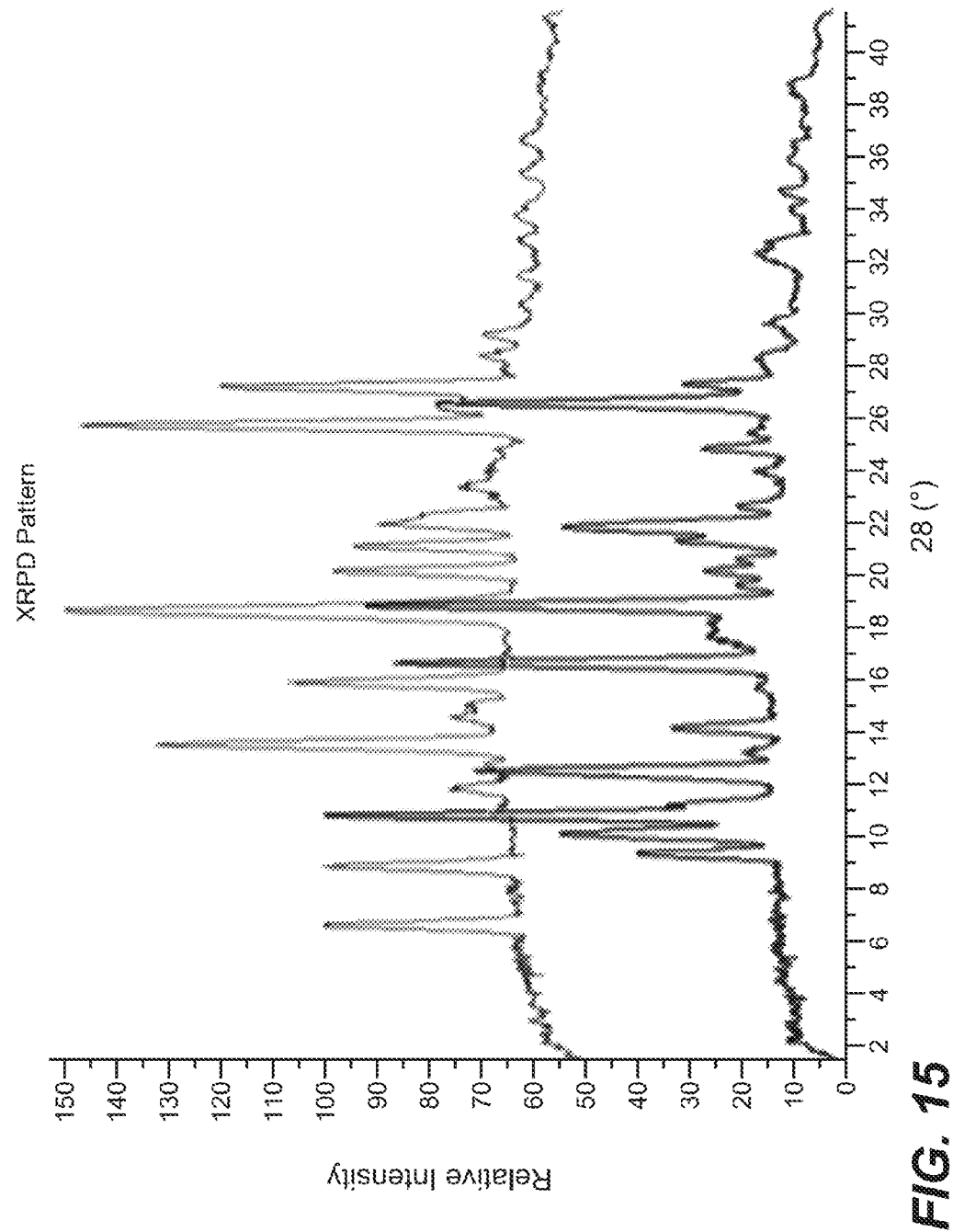
FIG. 15 shows an overlay of XRPD Data of GDC-0032 Form E (top) and Form B (bottom).

Form E was derived from 2,2,2-trifluoroethanol containing solvent systems and determined to be crystalline by XRPD. The XRPD data of Form E is given in FIG. 15. Thermal data of Form E indicated a weight loss of 18.1% up to a temperature of 160° C. (theoretical weight loss for mono-trifluoroethanolate: 17.8%). The weight loss was identified by TG-MS as 2,2,2-trifluoroethanol. DSC indicated the presence of a broad endotherm at 122° C. associated with desolvation as well as a sharp strong endotherm at 257° C. The endotherm at 257° C. is due to the melting of Form B. Single crystal structure elucidation confirmed that Form E is the mono-trifluoroethanolate.

Form F, Mono Acetonitrile Solvate

Figure 16:
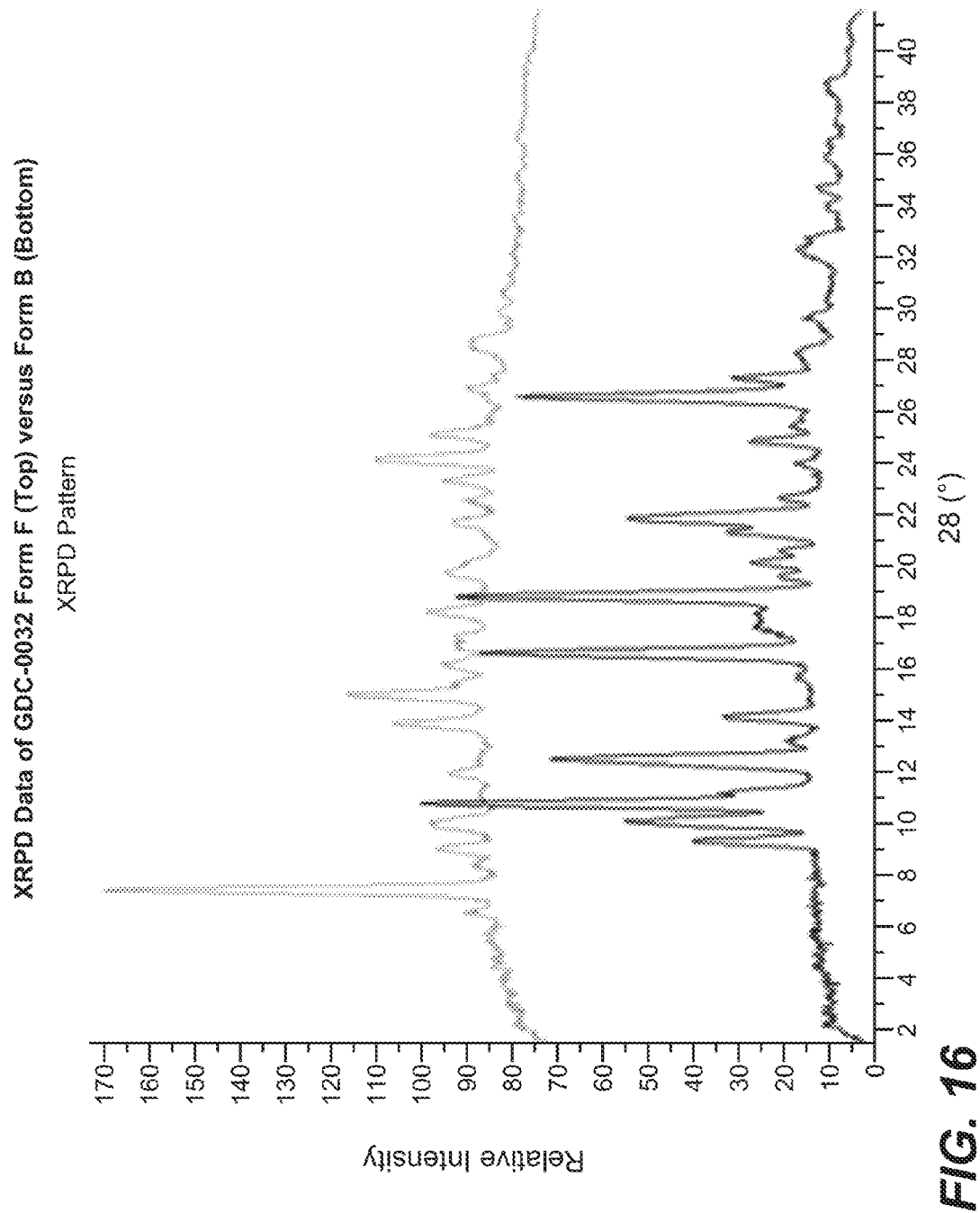
FIG. 16 shows an overlay of XRPD Data of GDC-0032 Form F (top) versus Form B (bottom).
Figure 17:
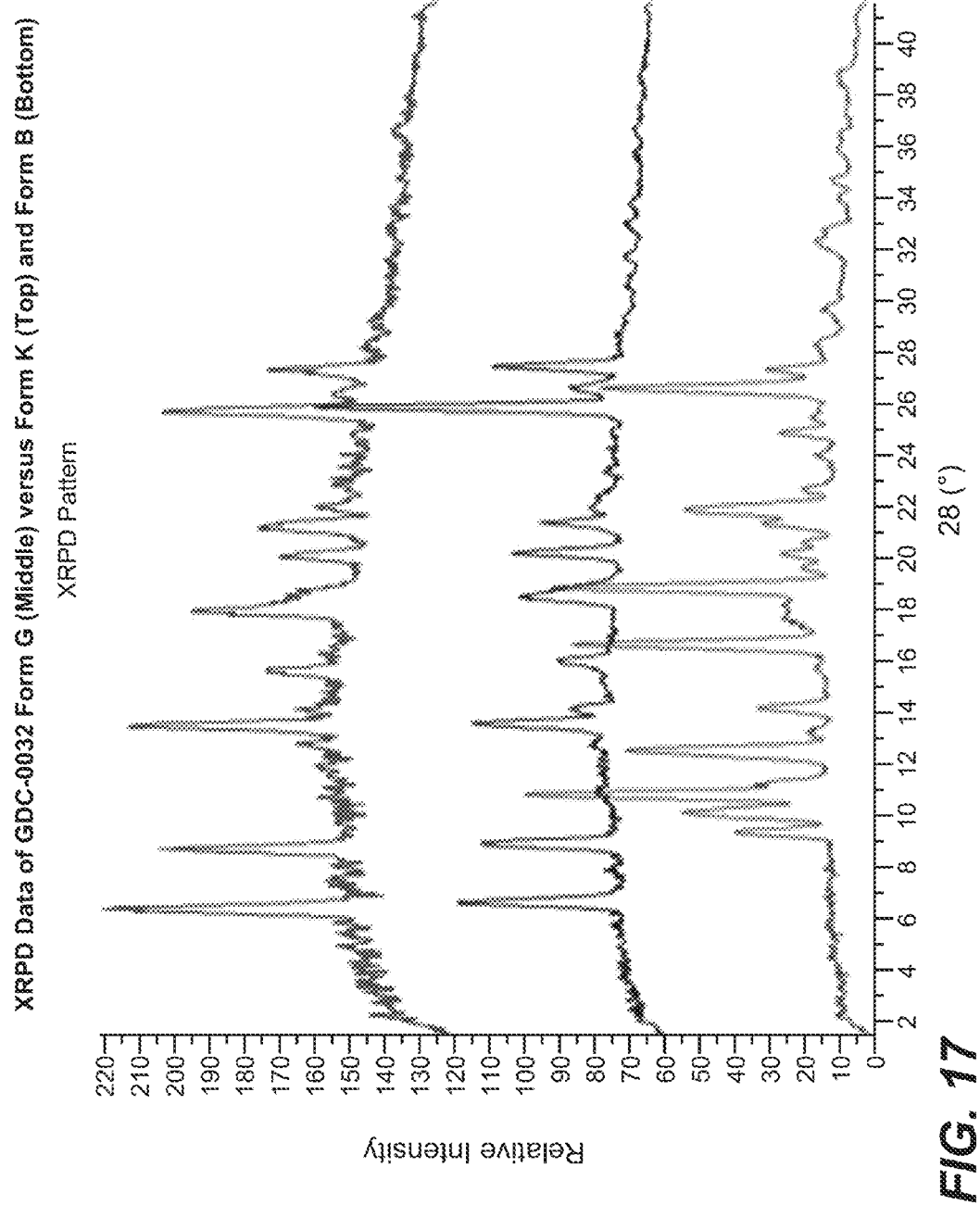
FIG. 17 shows an overlay of XRPD Data of GDC-0032 Form G (middle) versus Form K (top) and Form B (bottom).

Form F was derived from acetonitrile and ethanolic acetonitrile. Form F is crystalline as shown by XRPD. The XRPD data of Form F is shown in FIG. 16. TGA indicated a weight loss of 7.7% at a temperature up to 240° C. (theoretical weight loss for mono acetonitrile solvate: 8.2%). The weight loss was identified as ethanol and acetonitrile by TG-MS. DSC analysis indicated a broad endotherm at 124° C. associated with the weight loss in the TGA, followed by a strong endotherm at 252° C. is due to the melting of Form B. Single crystal structure elucidation confirmed that Form F is the mono-acetonitrile solvate. Although Form F is designated as the mono-acetonitrile solvate based on the single crystal data, the TG-MS data indicates that there may be an isomorphic mixed ethanol-acetonitrile solvate Form G, Mono-Ethanolate Form G was derived from ethanol and shown to be crystalline by XRPD (FIG. 17) and is essentially isomorphic with Form E, Form I, Form K, and Form L. Thermal data (TGA) indicated a weight loss of 9.6% at a temperature up to 160° C. (theoretical weight loss for monoethanolate: 9.1%). The weight loss was identified as ethanol by TG-MS. DSC analysis indicated a broad endotherm at 117° C. associated with the loss of ethanol followed by a strong endotherm at 256° C. In separate experiments, it was demonstrated that Form G converted to Form B upon heating under reduced pressure. Form G is the mono-ethanolate of GDC-0032 and is isomorphic with the trifluoroethanol solvate, Form E, which the crystal structure has been determined.

Form H, Mono-Chloroform Solvate

Form H is the mono-chloroform solvate of GDC-0032. This form was prepared from chloroform. The material is crystalline by XRPD as shown in Figure VV. TGA analysis indicated a weight loss of about 19.4% which corresponds to about 1 mole of chloroform. The structure of the solvate was identified by single crystal structure elucidation. Chloroform molecules occupy channels in the structure.

Form I, Mono-Tetrahydrofuran Solvate

Figure 18:
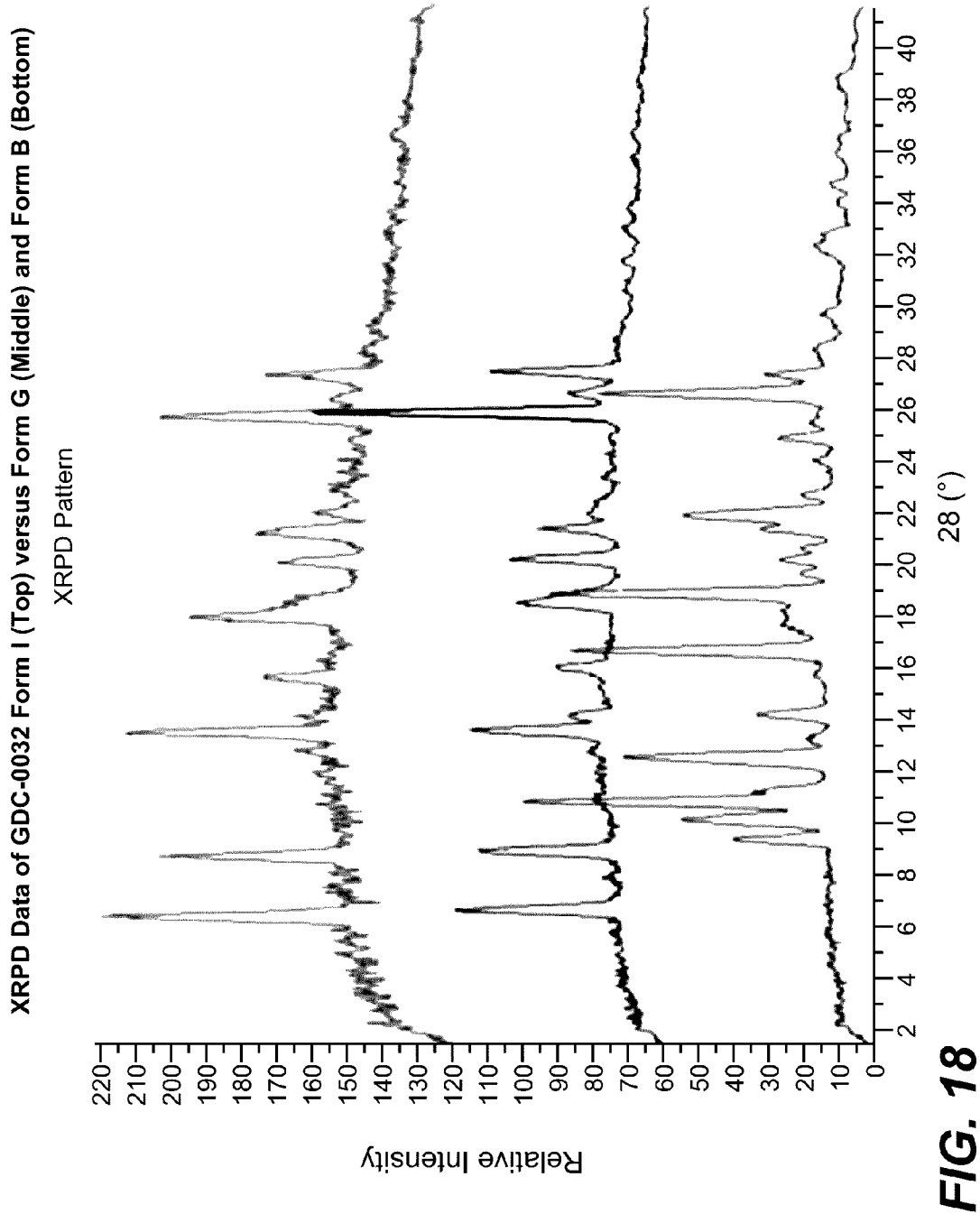
FIG. 18 shows an overlay of XRPD Data of GDC-0032 Form I (top) versus Form G (middle) and Form B (bottom).

Form I was derived from tetrahydrofuran (THF) and found to be crystalline by XRPD and essentially isomorphic with Form E and Form G (FIG. 18). Thermal data (TGA) indicated a weight loss of 15.0% at a temperature up to 180° C. (theoretical weight loss for mono-THF solvate: 13.5%). The weight loss was identified as THF by TG-MS. SDTA indicated a possible endotherm/exotherm combination at approximately 130° C. associated with weight loss and form conversion followed by a strong endotherm at 252° C. (max), the melt of Form B. Form I is the tetrahydrofuran solvate and is essentially isomorphic with Form E, Form G, Form K, and Form L.

Form J and Pattern J Materials

Figure 19:
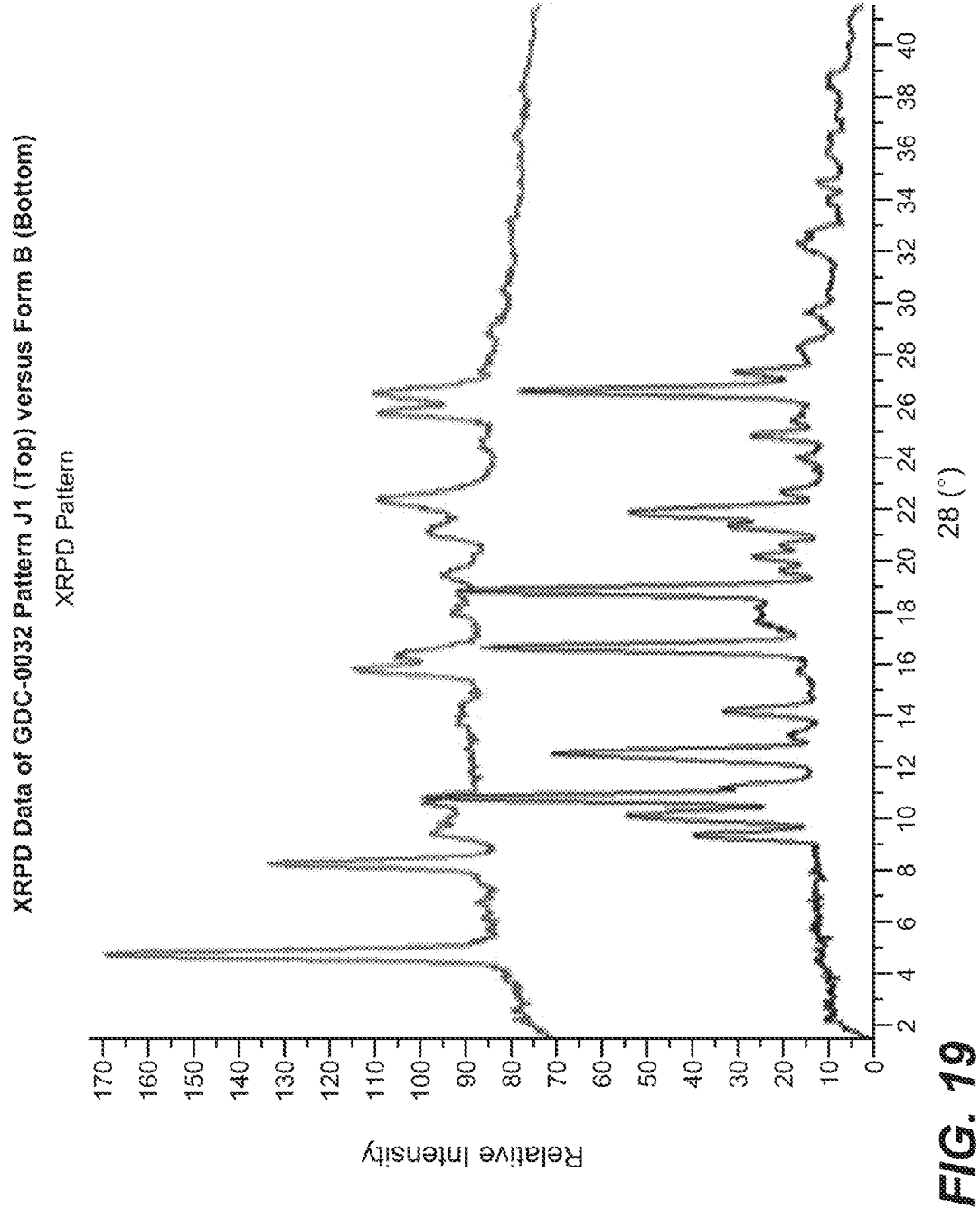
FIG. 19 shows an overlay of XRPD Data of GDC-0032 Pattern J1 (top) versus Form B (bottom).
Figure 20:
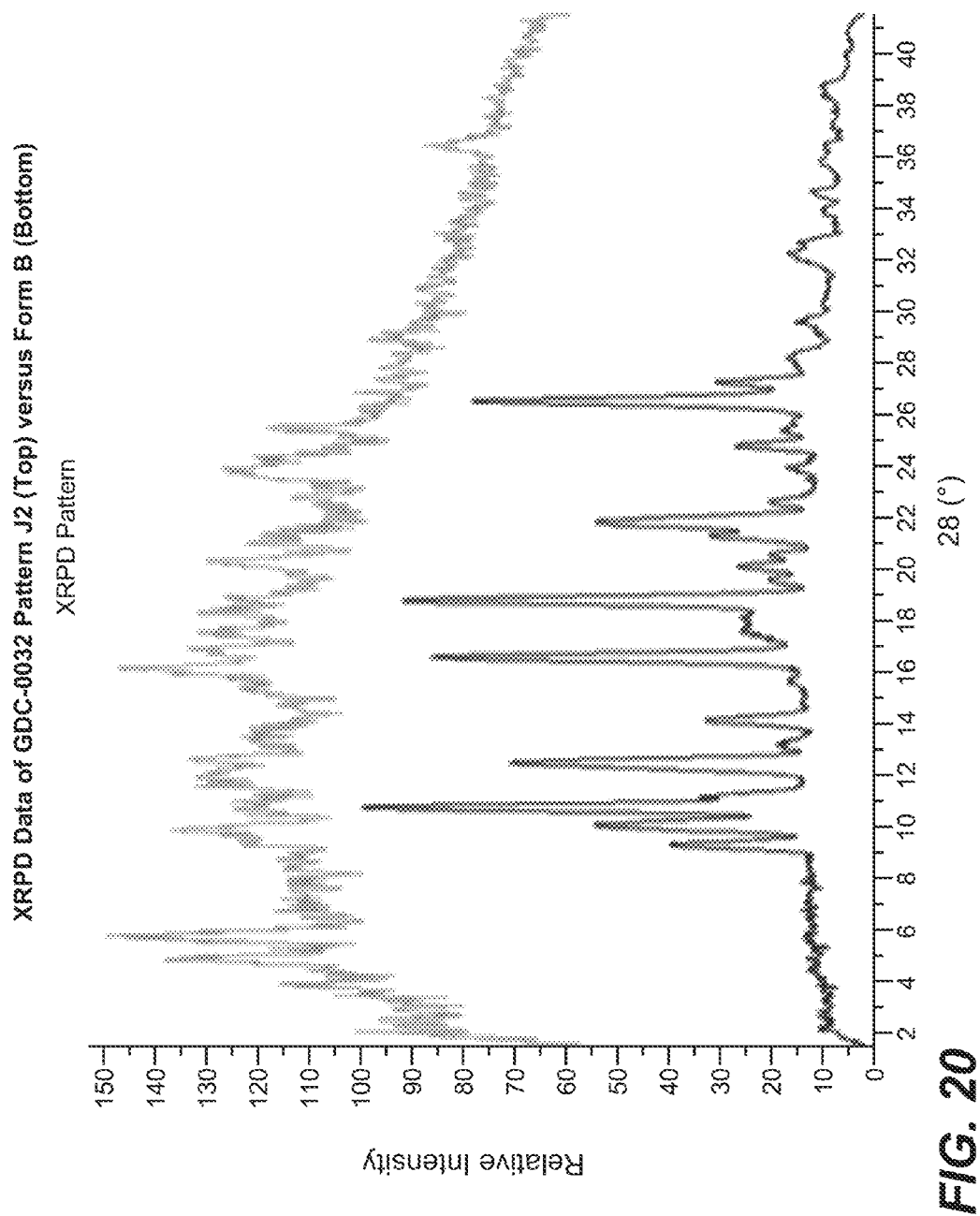
FIG. 20 shows an overlay of XRPD Data of GDC-0032 Pattern J2 (top) versus Form B (bottom).

Pattern J materials were derived from a cooling evaporation from acetone (Pattern J1), from acetone-water (Pattern J2), and from THF (Pattern J3). Pattern J material is crystalline by XRPD (FIGS. 19 and 20). Pattern J2 and Pattern J3 are isomorphic. The materials have been designated patterns due to the disorder in the powder patterns and the belief that the materials represent a partially desolvated structure. In addition, it is not clear what the relationship is between Form I and Pattern J3. Thermal data (TGA) for Pattern J1 indicated a weight loss of 6.8% at a temperature up to 240° C. (theoretical weight loss for hemi-acetone solvate: 5.9%, weight loss for mono-acetone solvate: 11.2%) with the majority of the weight loss occurring below 120° C. The weight loss was identified as acetone by TG-MS. TGA for Pattern J2 indicated a weight loss of 4.7% at a temperature up to 140° C. (theoretical weight loss for hemi-acetone solvate: 5.9%, weight loss for mono-acetone solvate: 11.2%) with the majority of the weight loss occurring below 100° C. The weight loss was identified as acetone by TG-MS. SDTA indicated a strong endotherm at 252° C. (max) for both patterns. The baseline in the SDTA for Pattern J2 is too noisy to draw conclusions as to potential form conversions. Pattern J3 was isolated from aqueous THF. No characterization data was collected. An isomorphic solvate (mixed solvate) of Pattern J containing THF may exist. Pattern J materials may consist of partial acetone solvates and a potential partial THF solvate.

Pattern K

Figure 21:
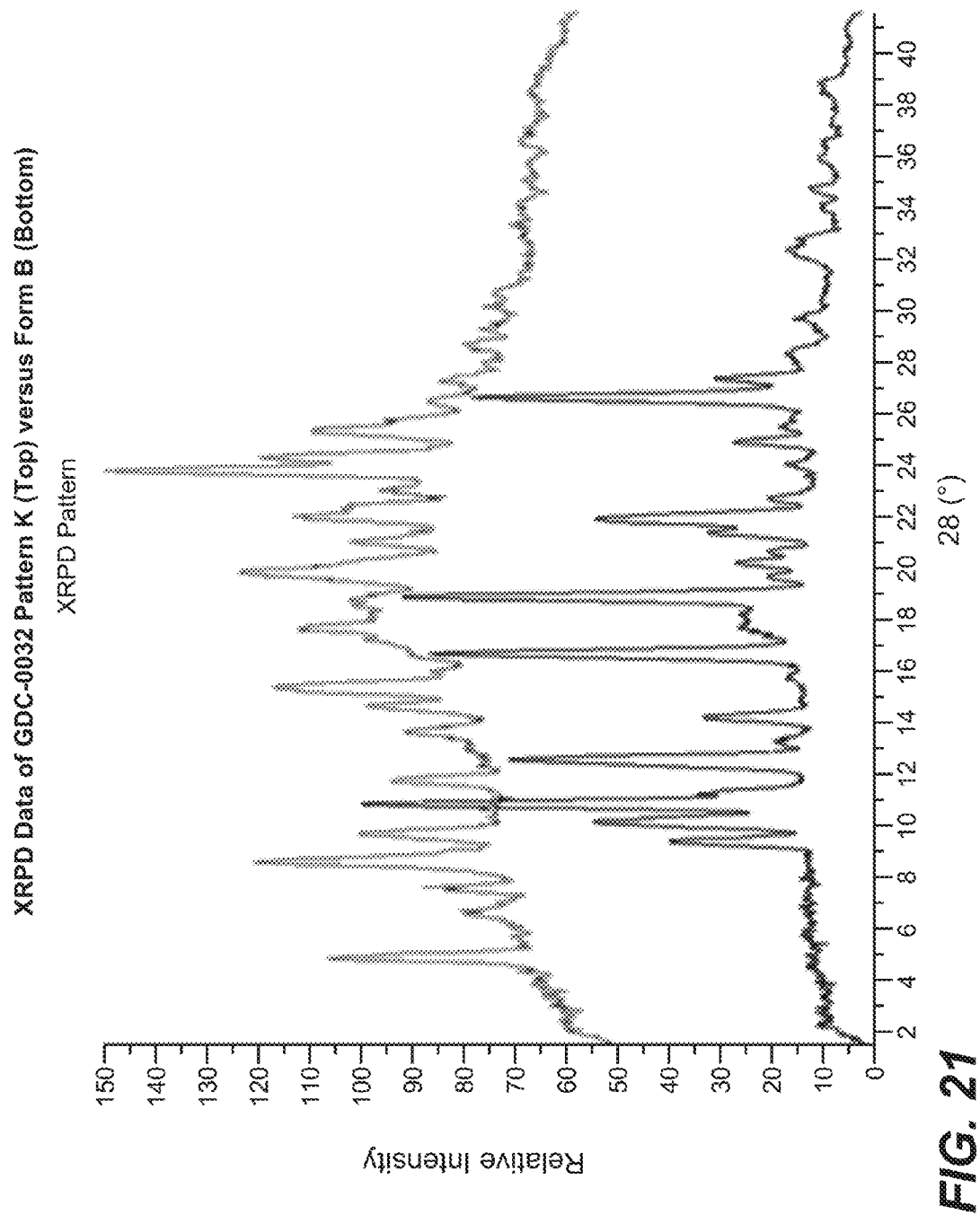
FIG. 21 shows an overlay of XRPD Data of GDC-0032 Pattern K (top) versus Form B (bottom).

Pattern K was isolated from 2,2,2-trifluoroethanol. The material is crystalline by XRPD but appears to be less crystalline than other forms (FIG. 21). There may be a small amount of Form E present. In addition, an amorphous or defected phase may be present. Therefore this material has not been designated as a form. TGA data indicated a weight loss of 19.8% at temperatures up to 240° C. with the majority of weight loss occurring before 140° C. The majority of the material was identified by TG-MS as mainly 2,2,2-trifluoroethanol (theoretical weight loss for mono-trifluoroethanolate: 17.8%). SDTA data indicated the presence of a broad endotherm at approximately 125° C. associated with weight loss and a strong endotherm at 252° C. (max), presumably due to the melt of Form B. The material appears to consist of a mono-trifluoroethanol solvate.

Form L Mono Isopropanol Solvate

Form L material was isolated from isopropanol. XRPD data indicates that this material is essentially isomorphic with Form E, Form G, Form I, and Form K. TGA and DSC data demonstrate a loss of solvent and conversion to orm B. Single crystal data is given in BBB and demonstrates that Form L is the ono-isopropanol solvate.

Pattern M

Pattern M materials were isolated from 1,2-dichloroethane (DCE)-nitromethane slurry and methyl ethyl ketone-heptane evaporation as well as a cooling experiment using 2-methyltetrahydrofuran (2-MeTHF)-heptane. There are slight differences between the powder patterns but it not known if these represent the quality of the data or if the differences represent differences between the structures of the solids. An additional material derived from 1-propanol-DCE has a similar powder pattern as the nitromethane-DCE derived material. Pattern M material from 1,2-dichloroethane-nitromethane was analyzed by TGA and DSC. TGA indicated a weight loss of 10.7% occurred by 132° C. The nature of the solvent was not identified (theoretical for hemi-dichloroethane solvate: 9.7%, theoretical for nitromethane solvate: 11.7%). DSC demonstrated a broad endotherm at 115° C. associated with weight loss in the TGA and a strong endotherm at 257° C. probably associated with the melt of Form B. Material prepared from 1-propanol was also analyzed by DSC. DSC data indicates the presence of a broad endotherm at 93° C. followed by a strong endotherm at 254° C. The broad endotherm is probably associated with weight loss but TGA data was not collected. Separate experiments using DCE and 2-Me-THF were conducted. DSC data for the DCE slurry indicated a very broad endotherm at 75° C. (onset) with two possible maxima at 85° C. and 104° C. followed by a strong endotherm at 256° C. DSC data from 2-MeTHF indicated a strong endotherm at 254° C. There may be weak transitions in the baseline but potential transitions have not been marked due to uncertainty due to the very small sample size. The broad endotherm for the DCE is probably associated with weight loss although TGA analysis was not conducted for either sample. Pattern M materials may represent a series of easily desolvated solvates.

Form N Nitromethane Solvate

Form N material was prepared from a long term slurry at 5° C. in nitromethane. XRPD analysis indicated the material was crystalline (Figure FF). TGA analysis indicated a 11.4% weight loss prior to 150° C. indicating the material is the mono-solvate of nitromethane. DSC analysis gave a endotherm at about 130° C. followed by the melting endotherm of Form B.

Form O carbontetrachloride mono-solvate

Form O was prepared by slurry at 60° C. in carbon tetrachloride. The material is crystalline by XRPD (Figure WW). TGA indicated a 24.4% weight loss prior to 150° C. indicating the form is a mono-carbontetrachloride solvate. DSC analysis gave an endotherm at about 143° C. and conversion to Form B.

Form P Propiontrile Mono-Solvate

Form P was prepared by slurry at 60° C. in propionitrile. The material is crystalline by XRPD (Figure WW). TGA indicated a 10.2% weight loss prior to 150° C. indicating the form is a mono-propionitrile solvate. DSC analysis gave an endotherm at about 130° C. and conversion to Form B.

Form Q 2-Methoxyethanol Mono-Solvate

Form Q was prepared by slurry at 22° C. in aqueous 2-methoxyethanol (5% water). The material is crystalline by XRPD (Figure WW). TGA indicated a 1'3.4% weight loss in two steps indicating the form is a mono-2-methoxyethanol solvate.

Form R Nitroethane Mono-Solvate

Form R was prepared by slurry at 22° C. in nitroethane. The material is crystalline by XRPD (Figure WW). TGA indicated a 13.3% weight loss prior to 150° C. indicating the form is a mono-nitroethane solvate. DSC analysis gave an endotherm at about 116° C. and conversion to Form B.

Form S 1,2-Dichloroethane ¼-Solvate

Form S was prepared by slurry at 22° C. in 1,2-dichloroethane. The material is crystalline by XRPD (Figure WW). TGA indicated a 5.0% weight loss prior to 180° C. indicating the form is a 1,2-dichloroethane ¼-solvate. DSC analysis gave an endotherm at about 179° C. and conversion to Form B.

Form T 1-Propanol Mono-Solvate

Form T was prepared by slurry at 5° C. in 1-propanol. The material is crystalline by XRPD (Figure WW). TGA indicated a 11.3% weight loss prior to 150° C. indicating the form is a 1-propanol mono-solvate. DSC analysis gave an endotherm at about 126° C. and conversion to Form B. Single crystal structure determination was also conducted and confirmed that Form T is the 1-propanol monosolvate (Figure VV and Table BB).

Form U Isobutanol Mono-Solvate

Form U was prepared by slurry at 20° C. in isobutanol. The material is crystalline by XRPD (Figure WW). TGA indicated a 13.6% weight loss prior to 150° C. indicating the form is a isobutanol mono-solvate. DSC analysis gave an endotherm at about 129° C. and conversion to Form B.

Form V 2-Methyltetrahydrofuran Mono-Solvate

Form T was prepared by slurry at 5° C. in 2-methyltetrahydrofuran. The material is crystalline by XRPD (Figure WW). TGA indicated a 15.2% weight loss prior to 150° C. indicating the form is a 2-methyltetrahydrofuran. DSC analysis gave an endotherm at about 120° C. and conversion to Form B. Single crystal structure determination was also conducted and confirmed that Form T is the 2-methyltetrahydrofuran monosolvate (Figure VV and Table BB). It is isomorphous with Form C.

Form W

Form W was prepared from a slurry in aqueous dioxane followed by vacuum drying. The material is crystalline by XRPD (Figure WW). DSC analysis gave an endotherm at about 191° C. and conversion to Form B.

Form X Mono-Hydrate

Form X was prepared from open storage of Form A or drying of Form A followed by exposure to ambient humidity. The material is crystalline by XRPD (Figure WW). DSC analysis gave an endotherm at about 140° C. and conversion to Form B. Form X reversibly converts to Form Y at low humidities (about 10-20% RH at 20° C.).

Form Y Hemihydrate

Form Y was prepared Form X at low humidity. The material is crystalline by XRPD (Figure WW). Form Y converts to Form B at about 120° C. by TGA.

Form Z Diisopropyl Ketone Mono-Solvate

Form Z was prepared by slurry at 5° C. in diisopropyl ketone. The material is crystalline by XRPD (Figure WW). DSC data indicated conversion to Form B occurs at about 110° C. Single crystal structure determination confirmed it is the mono-solvate. Form Z converts to Form B in the absence of diisopropyl ketone.

Form AA 1,4-Dioxane Hemi-Solvate

Form AA was prepared by long-term thermocycling at 20-25° C. in aqueous dioxane. Washing the solid with dioxane gave Form AA and washing with water gave Form D. The material is crystalline by XRPD (Figure WW). TGA indicated a 7.1% weight loss prior to 150° C. indicating the form is a dioxane hemi-solvate. Form AA is not stable in the absence of dioxane. Form AA converts to Form W after vacuum drying at 50° C. and about 5 millibar pressure.

Form AB

Form AB was prepared hot drying Form C or Form V at 50° C. and about 5 millibar pressure. The material is crystalline by XRPD (Figure WW).

Form AC Tetrahydrofuran Mono-Solvate

Form AC was prepared by slurry at 5° C. in tetrahydrofuran for 6 weeks. The material is crystalline by XRPD (Figure WW). TGA indicated a 12% weight loss prior to 150° C. indicating the form is a tetrahydrofuran mono-solvate. Form AC is not stable in the absence of tetrahydrofuran. Single crystal structure analysis was conducted and indicated that the material was the tetrahydrofuran mono-solvate (Figure VV and Table BB).

X-Ray Single-Crystal and Powder Diffraction Analysis

Analysis of X-ray Powder Diffraction (XRPD) patterns was conducted with commercially available, analytical software. XRPD is useful for fingerprinting of different crystalline phases, polymorphs, hydrates or solvates by their unique diffraction pattern. Along the abscissa (horizontal axis) is plotted the so-called 2Theta values—the series of angles between the incident and diffracted beams. The ordinate (vertical axis) records the intensity of the scattered X-ray registered by detector. The set of peaks act as a unique fingerprint of the crystallogaphic unit cell within a crystalline substance. The crystallographic unit cell is the smallest atomic-scale 3D fragment that is repeated periodically in three dimensions throughout the entire crystal. All crystalline substances are distinguished by their crystallographic unit cells (and therefore peak positions). By comparing measured peak positions with those held in a database, the crystalline substance may be identified uniquely. For pure substances, the positions of all peaks are generally a function of three parameters a, b, c and three angles alpha, beta, gamma ($\alpha$, $\beta$, $\gamma$) defining the elementary parallelepiped that constitutes the crystallographic unit cell.

Pharmaceutical Compositions and Formulations

A polymorph form of GDC-0032, Formula I, may be formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0032 in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of a polymorph form of GDC-0032 may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as lactose, sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Administration of Pharmaceutical Compositions

The pharmaceutical compositions of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, $18^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 1 mg to about 100 mg of a polymorph form of GDC-0032, such as about 3 mg to about 20 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

Polymorphs of GDC-0032 may differ by their in vivo bioavailability properties. Thus, the polymorphs disclosed herein may be useful in the preparation of pharmaceuticals with different characteristics for the treatment of hyperproliferative disorders such as cancer. This would allow generation of GDC-0032 preparations that have significantly different levels of adsorption with Cmax values from about 0.0 ng/ml to 5.0 .µg/ml. This leads to preparation of GDC-0032 compositions that are from negligibly to significantly adsorbed by subjects undergoing treatment. One embodiment of the invention is modulating the therapeutic action of GDC-0032 by selecting the proper polymorphic form, or mixture of forms, for treatment of a patient. For example, the most bioavailable polymorphic form of GDC-0032 can be selected from those disclosed herein, since it may be safer for the subject undergoing treatment.

The methods of the invention are useful for treating a hyperproliferative disorder such as cancer in a mammal (e.g., human) with a polymorph form of GDC-0032. For example, the methods are useful for diagnosing, monitoring, and treating multiple myeloma, lymphoma, leukemias, prostate cancer, breast cancer, hepatocellular carcinoma, lunch cancer, pancreatic cancer, and/or colorectal cancer in a mammal (e.g., human).

The methods of the invention are useful for inhibiting abnormal cell growth with a polymorph form of GDC-0032.

Therapeutic combinations of: (1) a polymorph form of GDC-0032 and (2) a chemotherapeutic agent are useful for treating diseases, conditions and/or disorders including, but not limited to, those characterized by activation of the PI3 kinase pathway. Accordingly, another aspect of this invention includes methods of treating diseases or conditions that can be treated by inhibiting lipid kinases, including PI3. In one embodiment, a method for the treatment of a solid tumor or hematopoietic malignancy comprises administering a therapeutic combination as a combined formulation or by alternation to a mammal, wherein the therapeutic combination comprises a therapeutically effective amount of GDC-0032, and a therapeutically effective amount of one or more chemotherapeutic agents selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole. Therapeutic combinations of: (1) a polymorph form of GDC-0032 and (2) a chemotherapeutic agent may be employed for the treatment of a hyperproliferative disease or disorder, including hematopoietic malignancy, tumors, cancers, and neoplastic tissue, along with pre-malignant and non-neoplastic or non-malignant hyperproliferative disorders. In one embodiment, a human patient is treated with a therapeutic combination and a pharmaceutically acceptable carrier, adjuvant, or vehicle, wherein GDC-0032, or metabolite thereof, of said therapeutic combination is present in an amount to detectably inhibit PI3 kinase activity.

Hematopoietic malignancies include non-Hodgkin's lymphoma, diffuse large hematopoietic lymphoma, follicular lymphoma, mantle cell lymphoma, chronic lymphocytic leukemia, multiple myeloma, AML, and MCL.

Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Combination Therapy

Polymorph forms of GDC-0032 may be employed in combination with certain chemotherapeutic agents for the treatment of a hyperproliferative disorder, including solid tumor or hematopoietic malignancy, along with pre-malignant and non-neoplastic or non-malignant hyperproliferative disorders. In certain embodiments, a polymorph form of GDC-0032 is combined with a chemotherapeutic agent in a single formulation as a single tablet, pill, capsule, or solution for simultaneous administration of the combination. In other embodiments, a polymorph form of GDC-0032 and the chemotherapeutic agent are administered according to a dosage regimen or course of therapy in separate formulations as separate tablets, pills, capsules, or solutions for sequential administration of a polymorph form of GDC-0032 and the chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole. The chemotherapeutic agent has anti-hyperproliferative properties or is useful for treating the hyperproliferative disorder. The combination of a polymorph form of GDC-0032 and chemotherapeutic agent may have synergistic properties. The chemotherapeutic agent of the pharmaceutical combination formulation or dosing regimen preferably has complementary activities to the polymorph form of GDC-0032, and such that they do not adversely affect each other. Such compounds of the therapeutic combination may be administered in amounts that are effective for the purpose intended. In one embodiment, a pharmaceutical formulation of this invention comprises GDC-0032 and a chemotherapeutic agent such as described herein. In another embodiment, the therapeutic combination is administered by a dosing regimen wherein the therapeutically effective amount of a polymorph form of GDC-0032 is administered in a range from twice daily to once every three weeks (q3wk), and the therapeutically effective amount of the chemotherapeutic agent is administered separately, in alternation, in a range from twice daily to once every three weeks.

Therapeutic combinations of the invention include a polymorph form of GDC-0032, and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole, for separate, simultaneous or sequential use in the treatment of a hyperproliferative disorder.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, the therapeutic combination may be combined with surgical therapy and radiotherapy, as adjuvant therapy. Combination therapies according to the present invention include the administration of a polymorph form of GDC-0032 and one or more other cancer treatment methods or modalities. The amounts of a polymorph form of GDC-0032 and the chemotherapeutic agent(s) and the relative timings of administration will be selected in order to achieve the desired combined therapeutic effect.

Articles of Manufacture

In another embodiment of the invention, an article of manufacture, or "kit", containing a polymorph form of GDC-0032 useful for the treatment of the diseases and disorders described above is provided. In one embodiment, the kit comprises a container comprising a polymorph form of GDC-0032. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold GDC-0032 or a formulation thereof which is effective for treating the condition and may have a sterile access port (for example, the container may be an intravenous solution bag or a vial having a stopper pierceable by a hypodermic injection needle). At least one active agent in the composition is a polymorph form of GDC-0032. The label or package insert indicates that the composition is used for treating the condition of choice, such as cancer. In one embodiment, the label or package inserts indicates that the composition comprising a Formula I compound can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of a polymorph form of GDC-0032 and, if present, the second pharmaceutical formulation. For example, if the kit comprises a first composition comprising GDC-0032 and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a polymorph form of GDC-0032, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a polymorph form of GDC-0032 contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a polymorph form of GDC-0032 and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

Example 1

Isolation and Physicochemical Characteristics of GDC-0032

GDC-0032 was prepared according to U.S. Pat. No. 8,242,104 and US 2014/0275523, each of which are incorporated by reference. A slurry of 1.15 kg, 2.50 moles crude 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (GDC-0032, Formula I) in MeOH (6 L, 5 vol), was charged to a 50 L glass reactor. Additional MeOH (24 L, 21 vol) was added to the mixture, which was then heated to 65° C. A homogenous mixture was obtained. Si-thiol (Silicycle, Inc., 0.23 kg, 20% wt) was added to the solution via the addition port and the mixture was stirred for 3 hours. It was then filtered warm via the Aurora filter (jacket temperature=60° C., polish filtered and transferred directly into a second 50 L reactor with reduced pressure. The solution was then heated back to 65° C. internal temperature (IT). The homogeneous solution was cooled down to 54° C. and GDC-0032 seeds (12 g, 1% wt) in MeOH (50 mL) were added with reduced pressure applied to the reactor. The mixture was then cooled down to 20° C. over 16 hours. The solids were then filtered via the Aurora filter and dried at 80° C. for 72 hours to give 921 g, 80% yield of GDC-0032 as a methanolate solvate (form A by XRPD,) and transferred to a pre-weighed charge-point bag.

In an isolator, the solids were slurred in IPAc (8 L, 7 vol) and transferred to a clean 10 L reactor. The mixture was stirred for 1 h at 60° C. (IT). The solids were then filtered via the Aurora system and dried at 80° C. (jacket) for 96 h. A sample of GDC-0032 was removed and analyzed by GC (IPAc=1%). To attempt more efficient drying, the API was transferred to two glass trays in an isolator and sealed with a drying bag before being dried in a vacuum oven set at 100° C. for 16 h. GC (IPC: Q12690V2) showed 1% solvent was still present. The process afforded 760 g (68% corrected yield, 68% wt, 99.9% purity by LC) of a white solid (form B by XRPD).

Crude GDC-0032 (340.7 g) was charged to a 2-L HDPE bottle and slurried with 0.8 L isoamylalcohol (IAA). The slurry was transferred to a 20 L reactor and diluted with 6.7 L round-bottom flask (22 vol total). The white slurry was heated until a solution was observed (internal temperature rose to 118° C. and then cooled to 109° C.). The solution was polish filtered (0.2 μM filter). A flask was equipped with overhead stirring and the filtrate was slurried in isoamyl alcohol (344 mL, 21 vol). The mixture was warmed to 95° C. (internal) until the solids dissolved. A slurry of charcoal (10 wt %, 0.16 g) and silicycle thiol (10 wt %, 0.16 g) in isoamyl alcohol (1 vol, 16 mL) was charged and the mixture was stirred at 90-95° C. for 1 h and then filtered (over Celite® pad). The clear amber colored solution was cooled to 73° C. (seeding temp range=70±5° C.) and a GDC-0032 seed (10 wt %, 0.16 g) was added. The temperature of the heating mantle was turned off and the mixture was allowed to cool to room temperature overnight with stirring (200 rpm). After 17 hr, the white solids were filtered starting with slow gravity filtration and then vacuum was applied. The solids were suction dried for 20 min with mixing until a free flowing powder was obtained. Crude weight prior to oven drying=16 g. The solids were oven-dried at 100° C. for 24 h and then sampled for testing. Drying continued at 100° C. for another 24 hr. 1H NMR (DMSO d6) δ8.38 (t), 8.01 (s), 7.87 (s), 7.44, 7.46 (d), 7.36 (s), 7.18 (br s), 6.81 (br s), 5.82 (m), 3.99 (s), 2.50 (s), 2.26 (s), 1.75 (s), 1.48, 1.46 (d).

GDC-0032 API is a white to off-white solid. It is crystalline as confirmed by the sharp peaks of its XRPD pattern and has a melting point of 258° C. Several physical forms of GDC-0032 free base, including an anhydrous form (Form B), several hydrates, and several solvates, have been identified to date. Form B has a melting point range of 256° C. to 258° C. Form B has been produced consistently in the API process to date. Form B does not exhibit any form change when exposed to high humidity for at least 6 months. In addition, no physical form conversion has been observed from the ongoing stability studies for the API. Hence, Form B was determined to be the most suitable crystalline form for further development. The reproducibility and stability of the crystalline form will be monitored during API synthesis and stability. GDC-0032 is non-hygroscopic, with less than 0.2% weight gain at 95% RH in the dynamic moisture sorption experiment. GDC-0032 is a weak base, with a pKa value of 3.19 and log P of 2.5, as determined by potentiometric titration.

Example 2

Solubility Assessment

The solubility behavior of GDC-0032 API is summarized as a Function of pH and in Different Buffers and Formulation Vehicles

| Buffer | Solubility (mg/mL) |
| --- | --- |
| 0.1N HCl, pH 1.1, at room temperature | 0.054 |
| 50 mM phosphate buffer, pH 6.5, at room temperature | 0.00072 |
| FaSSIF, pH 6.8, at 37° C. | 0.022 |
| FeSSIF, pH 5.0, at 37° C. | 0.27 |
| Water | 0.0015 |

Example 3

GDC-0032 Formulation and Tableting

Purified 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide I (GDC-0032) was dry granulation formulated in tablet form by the roller compaction method (He et al (2007) Jour. of Pharm. Sci., 96(5):1342-1355) with excipients including lactose, microcrystalline cellulose (AVICEL® PH 01, FMC BioPolymer, 50 μM particle), croscarmellose sodium (Ac-Di-Sol®, FMC BioPolymer), and magnesium stearate.

TABLE 7

Batch Formula for GDC-0032 Tablets, 3 mg API

| Ingredient | Function | Nominal Amount per Tablet (mg) | % (w/w) of Final Blend |
| --- | --- | --- | --- |
| GDC-0032[a] | Active ingredient | 3.0[a] | 3.0 |
| Microcrystalline Cellulose[b] Avicel PH 101 | Filler | 55.0[c] | 55.0 |
| Lactose Monohydrate | Filler | 37.0 | 37.0 |
| Croscarmellose Sodium Ac-Di-Sol | Disintegrant | 4.0 | 4.0 |
| Magnesium Stearate, Non-bovine | Lubricant | 1.0 | 1.0 |
| Total (Tablet Core) | | 100.0 | 100.0 |
| Opadry II White 85F18422[d] | Film coating system | 3.0[e] | NA |
| Purified Water, USP[f] | Coating vehicle | NA | NA |

[a]The amount of GDC-0032 is adjusted according to the potency of the API.
[b]The amount of microcrystalline cellulose is adjusted based on the actual amount of GDC-0032.

Example 4

Crystallization of GDC-0032

The solubility of GDC-0032 was determined in various solvents/solvent mixtures at two different temperatures: Ethanol absolute, Methanol, Isopropanol, Acetone, Ethyl Acetate, Isopropyl acetate, Tetrahydrofuran, 2-Butanone, Methanol/Water (50/50), 2,2,2-Trifluoroethanol (TFE), 2-Butanone, TFE/Ethyl acetate (50/50), TFE/Acetone (50/50), TFE/Water (50/50), Acetonitrile, Acetonitrile/water (50/50), Acetone/water (50/50), Tert-butyl methyl ether, n-Heptane, Ethanol/Ethyl acetate (50/50), Ethanol/Acetone (50/50), Methanol/water (90/10), Ethanol/Acetonitrile (50/50). GDC-0032 was soluble in all except for Ethyl Acetate, Isopropyl acetate, Tetrahydrofuran, Tert-butyl methyl ether, and n-Heptane.

For each experiment, approximately 5-10 mg of material was weighed in 40 mL vials. In the case of 2,2,2-trifluoroethanol (TFE), about 40 mg was used due to the high solubility of GDC-0032 in this solvent. In each vial, the solvent was added to the solid in steps of 50 μL until dissolution or until a minimum concentration of 0.2 mg/mL was reached. Dissolution was assessed visually at two temperatures, room temperature (RT) and a higher temperature ($T_{max}$ 50 or 70° C., selected such that the boiling point of the solvent was higher than $T_{max}$). Solubility was measured by HPLC for suspensions.

Example 5

Crystallization Screen

A high throughput crystallization screen was conducted. GDC-0032 was dissolved in N,N-dimethyl formamide at 65° C. The DMF solution was dispensed into four 96 well plates. The solvent was evaporated and replaced with 16 different pure solvents and 80 solvent mixtures. The solvent mixtures were generated by adding a gradient of water, ethanol, 1,2-dichloroethane, or heptane. Typical ratios are 800:0, 640:160, 480:320, 320:480, 160:640, 0:800. One plate was allowed to evaporate under nitrogen at room temperature (evaporation). Cyclopentyl methyl ether was added as an antisolvent to the wells in a second plate (precipitation). Two plates were heated to 65° C. and one plate was allowed to cool to 10° C. over 12 hours (cooling plate) and the second plate was maintained at 65° C. for 1 week (slurry at 65 plate). The solvents were decanted and the resulting solids analyzed by polarized light microscopy (PLM). Solids which appeared crystalline by PLM were analyzed by X-ray powder diffraction (XRPD). Materials that had different powder patterns were then analyzed by Raman spectroscopy.

Single Crystal: Single crystal structure solutions were obtained for Form A, Form B, Form C, Form E, and Form K.

Thermocycling of GDC-0032 in organic solvents: Approximately 60 mg of starting material was weighed in 8 mL vials. Four slurries were prepared in TFE/ethyl acetate (50/50), methanol, ethanol and acetone. The slurries were thermo-cycled between 60° C. and 20° C. or between 50° C. and 20° C. The cooling and heating rates were 10° C./hr and the holding time at each temperature was 30 min. The cycle was repeated about five times. At the end of the thermocycling, insufficient solids were observed and the solvents were evaporated. The solids were measured by XRPD and digital imaging.

Seeding experiments: Experiments with 10 and 20% w/w seeds were performed at 8 mL scale using 60 mg of starting material. Two slurries in TFE/ethyl acetate (50/50) and methanol were prepared and heated to 60° C. After one hour of equilibration time, the slurries were filtrated at 60° C. Subsequently seeds were added to the filtrate at 60° C. and the mixture was cooled to 5° C. with a cooling rate of 5° C./h and aged at that temperature for 10 hours. The solids were separated and dried and the mother liquors were evaporated. All solids were analyzed by XRPD and digital imaging.

Cooling-evaporation experiments with hot filtration: Two slurries were prepared in ethanol and acetone at 50° C., and following one hour of equilibration time, the slurries were filtrated at the same temperature. The saturated solutions were subsequently cooled to 5° C. with a cooling rate of 5° C./h and aged overnight at this temperature. No solids were observed after ageing and the solvents were evaporated. The obtained solids were analyzed by XRPD and digital imaging.

Solubility of GDC-0032 in methanol at high temperature: Solubility of GDC-0032 in methanol at 45° C. and 55° C. was measured. Two slurries were prepared with approximately 15 mg of starting material and 500 mL of methanol. The slurries were subsequently placed in two ovens, at 45° C. and 55° C. each. After 24 hours of equilibration the two slurries were visually checked. In both cases the dissolution was not complete. The solids were separated from the mother liquor and were harvested both wet and dried for XRPD and digital imaging. The mother liquor was evaporated and the solids were also analyzed by XRPD and digital imaging.

Thermocycling of GDC-0032 in organic solvents with seeding was performed in six solvents in which saturated solutions were prepared at 60° C. (for acetone the maximum temperature applied was 50° C.). After a few hours of equilibration time, the slurries were filtrated at Tmax. After filtration, a few mg of starting material were added to each saturated solution and then thermo-cycled from Tmax to 20° C. with a cooling rate of 5° C./h and back to Tmax with a heating rate of 10° C./h with a holding time at Tmax and 20° C. of 15 min. No stirring was applied to these experiments. The cycles were repeated from 13 times to 17 times. After the thermo-cycling applied to the experiments the solutions were ageing at 5° C. for 3 days. At the end of the experiments it was considered that the precipitated solids were not sufficient for analytics and it was decided to slowly evaporate the solvents. The obtained solids were analyzed by XRPD, digital imaging, Malvern particle size analyzer and microscopy.

Vapor diffusion into solutions of GDC-0032 with seeding using 3 solvents and 3 anti-solvents were performed. For these experiments three saturated solutions were prepared in the three solvents at room temperature. After a few hours of equilibration time, the slurries were filtrated at room temperature in 8 mL vials. A few mg of starting material were added to these saturated solutions (seeds). Then the 8 mL vials with the seeds were placed in a 40 mL vial containing 3 mL of anti-solvent. The solutions were exposed for two weeks to the anti-solvent vapors. At the end of the experiments it was considered that the precipitated solids were not sufficient for analytics and it was decided to slowly evaporate the solvents. The obtained solids were analyzed by XRPD and digital imaging.

Preparation of Form A: Methanol, 2 mL, was added to GDC-0032, 189 mg. The suspension was heated to 65° C. for 30 minutes and then allowed to cool to 3° C. and stirred overnight. The solid was collected via filtration and isolated while still wet with solvent.

Preparation of Form A: A suspension containing 585.4 mg of compound (lot 978822, Form B) and 10 mL of methanol was agitated in a closed glass vial at ambient temperature for 6 days. The product was sedimented by centrifugation and the mother liquor was removed with a pipette. The crystals were analyzed in wet stage.

Preparation of Form B single crystal: Crystals suitable for single crystal structure determination for GDC-0032 were obtained by dissolution of GDC-0032 in ethyl acetate followed by vapor diffusion using pentane.

Preparation of Form C: GDC-0032 (103.8 mg) was partially dissolved in hot isoamyl alcohol (5 mL) at 90° C. The suspension was slowly allowed to cool to 5° C. and slurried at 5° C. for 2 days. The solid was collected by filtration and analyzed while damp with solvent in a sealed X-ray holder.

Preparation of Form C: In a closed glass vial 4.98 g of compound (lot BS1302SA01, Form B) were dissolved in 166.7 g of an isoamyl alcohol at 95° C. While agitating, the clear solution was rapidly cooled by immersing the vial into a water/ice bath. The resulting suspension was agitated for 9 days at 5° C. The crystals were isolated by filtration and dried at ambient conditions for 4 days.

Preparation of Form D: GDC-0032 (98.7 mg) was slurried in aqueous n-butanol (1:1 v: v, 1 mL) for 3 days. The solid was collected by microcentrifugation through a filter in a sealed container. XRPD analysis was collected on the sample while it was still wet with solvent.

Preparation of Form D: In a closed glass vial 388.7 mg of compound (lot 978822, Form B) were dissolved in 7.4 mL of an n-propanol/water mixture (10%-v/v water) at 75° C. The clear solution was linearly cooled to 22° C. within 8 h. After picking of crystals for single crystal X-ray analysis, the reminder of the suspension was agitated before the crystals were isolated by filtration and dried at 40° C./400 mbar for 16 h.

Preparation of Form E: In a closed glass vial 521.1 mg of compound (lot 978822, Form B) were dissolved in 1.5 mL of trifluorethanol at 75° C. After controlled cooling the clear solution stored at 10° C. Single crystals were obtained after 8 days. After picking of crystals for single crystal X-ray analysis, the reminder of the suspension was agitated at ambient temperature overnight, before the vial was opened to allow complete evaporation of the solvent at ambient conditions. The crystals were analyzed without further processing.

Preparation of Form E: A slurry of GDC-0032 (59.6 mg) in 2,2,2-trifluoroethanol (1 mL) and ethyl acetate (1 mL) was heated to 60° C. and held there or one hour. The slurry was filtered while hot, GDC-0032 Form B (6 mg) was added and the suspension cooled to 5° C. at a rate of 5° C./hour and held there for 10 hours. The solids were collected and analyzed by XRPD.

Preparation of Form F: A saturated solutions of GDC-0032 in acetonitrile was prepared at 60° C. by slurrying GDC-0032 Form B (30 mg) in acetontrile (7 mL) at 60° C. After a few hours of equilibration time, the slurries were filtrated at $T_{max}$. After filtration a few mg of GDC-0032 were added to each saturated solution and then thermo-cycled from $T_{max}$ to 20° C. with a cooling rate of 5° C./h and back to $T_{max}$ with a heating rate of 10° C./h with a holding time at both $T_{max}$ and 20° C. of 15 min. No stirring was applied to these experiments. The cycles were 13 times. After the thermo-cycling applied to the experiments the solutions were aged at 5° C. for 3 days. At the end of the experiments it was considered that the precipitated solids were not sufficient for analytics and it was decided to slowly evaporate the solvents. The obtained solids were analyzed by XRPD, digital imaging, Malvern particle size analyzer and microscopy.

Preparation of Form F: A suspension containing 400.2 mg of compound (lot 978822, Form B) and 7.2 mL of acetonitrile was agitated in a closed glass vial at ambient temperature for 24 days. The product sedimented by centrifugation and the mother liquor was removed with a pipette. The crystals were dried at 50° C./5 mbar for 2 days.

Preparation of Form G: GDC-0032 Form B (11.9 mg) was dissolved in absolute ethanol (5.5 mL0 and evaporated under vacuum at room temperature.

Preparation of Form H: GDC-0032 (20.5 mg) was dissolved in chloroform (600 µL) at room temperature. The solution was left to stand for 6 months while the solution slowly evaporated to give a crystal suitable for structure analysis.

Preparation of Form H: A suspension containing 385.8 mg of compound (lot 978822, Form B) and 6.9 mL of chloroform was agitated in a closed glass vial at ambient temperature for 24 days. The product was sedimented by centrifugation and the mother liquor was separated with a pipette. The mother liquor was allowed to evaporate completely at ambient conditions. The crystals were analyzed without further processing.

Preparation of Form J: A suspension containing 457.6 mg of compound (lot 978822, Form B) and 8.2 mL of dioxane was agitated in a closed glass vial at ambient temperature for 24 days. The product was sedimented by centrifugation and the mother liquor was removed with a pipette. The crystals were dried at 50° C./5 mbar for 15 minutes.

Preparation of Form K: In a closed glass vial 302.7 mg of compound (lot 978822, Form B) were dissolved in 5.4 mL of acetic acid at ambient temperature. To the clear solution 4.2 mL of n-heptane were added. The resulting suspension was agitated overnight at ambient temperature. The product was sedimented by centrifugation and the mother liquor was removed with a pipette. The product was sedimented by centrifugation and the mother liquor was removed with a pipette. The crystals were analyzed in wet stage.

Preparation of Form L: In a closed glass vial 199.7 mg of compound (lot 978822, Form B) were dissolved in 12.0 mL of iso-propanol at 90° C. The clear solution was linearly cooled to 22° C. within 8 h. After picking of crystals for single crystal X-ray analysis, the reminder of the suspension was agitated at ambient temperature overnight. The crystals were analyzed without further processing.

Preparation of Form M: A suspension containing 470.5 mg of compound (lot 978822, Form B) and 8.5 mL of dichloromethane was agitated in a closed glass vial at 5° C. for 15 days. The product was sedimented by centrifugation and the mother liquor was removed with a pipette. The crystals were dried at ambient conditions overnight.

Preparation of Form N: A suspension containing 389.5 mg of compound (lot 978822, Form B) and 7.0 mL of nitroethane was agitated in a closed glass vial at ambient temperature for 24 days. The product was sedimented by centrifugation and the mother liquor was removed with a pipette. The crystals were dried at 50° C./5 mbar for 2 days.

Preparation of Form O: A suspension containing 480.7 mg of compound (lot 978822, Form B) and 8.7 mL of carbon tetrachloride was agitated in a closed glass vial at 60° C. for 14 days. The product was sedimented by centrifugation and the mother liquor was removed with a pipette. The crystals were dried at 50° C./5 mbar for 17 h.

Preparation of Form P: A suspension containing 469.8 mg of compound (lot 978822, Form B) and 8.5 mL of propionitrile was agitated in a closed glass vial at 60° C. for 14 days. The product was sedimented by centrifugation and the mother liquor was removed with a pipette. The crystals were dried at 50° C./5 mbar for 17 h.

Preparation of Form Q: A suspension containing 488.6 mg of compound (lot 978822, Form B) and 8.8 mL of 2-methoxyethanol/water 85/15 (v/v) was agitated in a closed glass vial at ambient temperature for 24 days. The product was sedimented by centrifugation and the mother liquor was removed with a pipette. The crystals were dried at 50° C./5 mbar for 15 minutes.

Preparation of Form R: A suspension containing 389.5 mg of compound (lot 978822, Form B) and 7.0 mL of nitroethane was agitated in a closed glass vial at ambient temperature for 24 days. The product was sedimented by centrifugation and the mother liquor was removed with a pipette. The crystals were dried at 50° C./5 mbar for 2 days.

Preparation of Form S: A suspension containing 387.2 mg of compound (lot 978822, Form B) and 7.0 mL of 1,2-dichloroethane was agitated in a closed glass vial at ambient temperature for 24 days. The product was sedimented by centrifugation and the mother liquor was removed with a pipette. The crystals were dried at ambient conditions.

Preparation of Form T: A suspension containing 397.5 mg of compound (lot 978822, Form B) and 7.2 mL of n-propanol was agitated in a closed glass vial at 5° C. for 6 weeks. The product was sedimented by centrifugation and the mother liquor was removed with a pipette. The crystals were dried at 40° C./400 mbar 5 h in the presence of n-propanol.

Preparation of Form U: In a closed glass vial 235.6 mg of compound (lot 978822, Form B) were dissolved in 9.4 mL of i-butanol at 85° C. The clear solution was linearly cooled to 40° C. within 8 h. After picking of crystals for single crystal X-ray analysis, the reminder of the suspension was stored at ambient temperature for 4 days. The solvent was completely evaporated at ambient conditions and the crystals were dried at 50° C./5 mbar for 27 h.

Preparation of Form V: A suspension containing 498.1 mg of compound (lot 978822, Form B) and 9.0 mL of 2-methyltetrahydrofuran was agitated in a closed glass vial at 20° C. for 6 weeks. The crystals were harvested by centrifugal filtration and analyzed in wet state.

Preparation of Form W true polymorph: A suspension containing 330 mg of compound (lot 978822, Form B) and 6.0 mL of dioxane/water 1/1 (v/v) was agitated in a closed glass vial at 20 to 25° C. for 5 weeks. The crystals were isolated by centrifugal filtration and dried at 70° C./5 mbar for 2 days.

Preparation of Form X hydrate: A suspension containing 498.9 mg of compound (lot 978822, Form B) and 10 mL of methanol was agitated in a closed glass vial at ambient temperature for 4 days. The product was sedimented by centrifugation and the mother liquor was removed with a pipette. The crystals were dried at 50° C./5 mbar 2 days.

Preparation of Form Y: X hemihydrate: A suspension containing 498.9 mg of compound (lot 978822, Form B) and 10 mL of methanol was agitated in a closed glass vial at ambient temperature for 4 days. The product was sedimented by centrifugation and the mother liquor was removed with a pipette. The crystals were dried at 50° C./5 mbar 2 days and then stored at ambient temperature over an aqueous LiCl suspension (11%-RH) for 20 days. During analysis the surrounding humidity was kept at 11%-RH.

Preparation of Form Z: A suspension containing 488.1 mg of compound (lot 978822, Form B) and 8.8 mL of diisopropyl ketone was agitated in a closed glass vial at 5° C. for 15 days. The product was sedimented by centrifugation and the mother liquor was removed with a pipette. The crystals were dried at ambient conditions.

Preparation of Form AA dioxane hemi-solvate: A suspension containing 426.0 mg of compound (lot 978822, Form B) and 7.7 mL of dioxane/water 1/1 (v/v) was agitated in a closed glass vial at ambient temperature for 5 weeks. The product was sedimented by centrifugation and the mother liquor was removed with a pipette. The crystals dried at ambient temperature/500 mbar for 30 minutes.

Preparation of Form AB true polymorph: In a closed glass vial 4.98 g of compound (lot BS1302SA01, Form B) were dissolved in 166.7 g of an isoamyl alcohol at 95° C. While agitating, the clear solution was rapidly cooled by immersing the vial into a water/ice bath. The resulting suspension was agitated for 9 days at 5° C. The crystals were isolated by filtration and dried at 50° C./5 mbar for 2 days.

Preparation of Form AC: In a closed glass vial 200.8 mg of compound (lot 978822, Form B) were dissolved in 7.7 mL of tetrahydrofuran at 75° C. The clear solution was linearly cooled to 20° C. within 10 h. After picking of crystals for single crystal X-ray analysis, the reminder of the suspension was agitated at ambient temperature overnight. The crystals were analyzed without further processing.

Example 6

XRPD Analytical Methods

TABLE 8

Crystal Data and Data Collection Parameters for GDC-0032 Form B

| | |
|---|---|
| formula | $C_{24}H_{28}N_8O_2$ |
| formula weight | 460.54 |
| space group | P-1 (No. 2) |
| a, Å | 9.7944(14) |
| b, Å | 10.4767(11) |
| c, Å | 12.5994(17) |
| α, (alpha) deg | 96.145(10) |
| β, (beta) deg | 95.749(11) |
| γ, (gamma) deg | 115.072(9) |
| V, Å$^3$ | 1149.0(3) |
| Z | 2 |
| $d_{calc}$, g cm$^{-3}$ | 1.331 |
| crystal dimensions, mm | 0.20 × 0.11 × 0.08 |
| temperature, K | 150. |

TABLE 8-continued

Crystal Data and Data Collection Parameters for GDC-0032 Form B

| | |
|---|---|
| radiation (wavelength, Å) | Cu K$_\alpha$ (1.54184) |
| monochromator | confocal optics |
| linear abs coef, mm$^{-1}$ | 0.725 |
| absorption correction applied | empirical[a] |
| transmission factors: min, max | 0.90, 0.94 |
| diffractometer | Rigaku RAPID-II |
| h, k, l range | 0 to 11 −12 to 11 −15 to 15 |
| 2θ range, deg | 7.15-140.65 |
| mosaicity, deg | 0.56 |
| programs used | SHELXTL |
| F$_{000}$ | 488.0 |
| weighting $1/[\sigma^2(Fo^2) + (0.0810P)^2 + 0.5152P]$ where $P = (Fo^2 + 2Fc^2)/3$ | |
| data collected | 18706 |
| unique data | 4029 |
| R$_{int}$ | 0.042 |
| data used in refinement | 4029 |
| cutoff used in R-factor calculations | $F_o^2 > 2.0\sigma(F_o^2)$ |
| data with I > 2.0σ(I) | 3257 |
| number of variables | 330 |
| largest shift/esd in final cycle | 0.00 |
| R(F$_o$) | 0.060 |
| R$_w$(F$_o^2$) | 0.158 |
| goodness of fit | 1.061 |

[a]Otwinowski Z. & Minor, W. Methods Enzymol., (1997), 276, 307.

TABLE 9

Crystal Data and Data Collection Parameters for GDC-0032 Form A

| | |
|---|---|
| Crystal group | monoclinic |
| Formula | $C_{25}H_{32}N_8O_3$ ($C_{24}H_{28}N_8O_2$ + $CH_3OH$) |
| formula weight | 492.59 |
| space group | P 1 21/c 1 (No. 14) |
| a, Å | 16.1478(8) |
| b, Å | 10.9055(4) |
| c, Å | 14.9317(7) |
| γ, (gamma), deg | 103.399(3) |
| V, Å$^3$ | 2557.9(2) |
| Z | 4 |
| $d_{calc}$, g cm$^{-3}$ | 1.279 |
| crystal dimensions, mm | 0.20 × 0.20 × 0.08 |
| temperature, K | 295. |
| radiation (wavelength, Å) | Cu K$_\alpha$ alpha (1.54184) |
| monochromator | confocal optics |
| linear abs coef, mm$^{-1}$ | 0.714 |
| absorption correction applied | empirical |
| transmission factors: min, max | 0.81, 0.94 |
| diffractometer | Rigaku RAPID-II |
| h, k, l range | −18 to 17 −12 to 0 0 to 17 |
| 2θ range, deg | 5.63-126.63 |
| mosaicity, deg | 0.42 |
| programs used | SHELXTL |
| F$_{000}$ | 1048.0 |
| weighting $1/[\sigma^2(Fo^2) + (0.0715P)^2 + 0.8020P]$ where $P = (Fo^2 + 2Fc^2)/3$ data collected | 25557 |
| unique data | 4138 |
| R$_{int}$ | 0.035 |
| data used in refinement | 4138 |
| cutoff used in R-factor calculations | $Fo^2 > 2.0\sigma(F_o^2)$ |
| data with I > 2.0σ(I) | 3504 |
| number of variables | 343 |
| largest shift/esd in final cycle | 0.00 |
| R(F$_o$) | 0.047 |
| R$_w$(F$_o^2$) | 0.126 |
| goodness of fit | 1.042 |

TABLE 10

Crystal Data and Data Collection Parameters for GDC-0032 Form D

| | |
|---|---|
| formula | $C_{24}H_{30}N_8O_3$ ($C_{24}H_{28}N_8O_2$ + $H_2O$) |
| formula weight | 478.56 |
| space group | P 1 21/c 1 (No. 14) |
| a, Å | 5.80760(10) |
| b, Å | 20.2279(4) |
| c, Å | 20.9696(15) |
| b, deg | 91.265(6) |
| V, Å$^3$ | 2462.82(19) |
| Z | 4 |
| $d_{calc}$, g cm$^{-3}$ | 1.291 |
| crystal dimensions, mm | 0.20 × 0.18 × 0.13 |
| temperature, K | 150. |
| radiation (wavelength, Å) | Cu K$_\alpha$ alpha (1.54184) |
| monochromator | confocal optics |
| linear abs coef, mm$^{-1}$ | 0.727 |
| absorption correction applied | empirical |
| transmission factors: min, max | 0.80, 0.91 |
| diffractometer | Rigaku RAPID-II |
| h, k, l range | −6 to 6 −23 to 24 −23 to 24 |
| 2q range, deg | 4.21-133.16 |
| mosaicity, deg | 1.25 |
| programs used | SHELXTL |
| $F_{000}$ | 1016.0 |
| weighting $1/[s^2(Fo^2) + (0.0724P)^2 + 0.9585P]$ where P = (Fo$^2$ + 2Fc$^2$)/3 data collected | 22410 |
| unique data | 4322 |
| $R_{int}$ | 0.024 |
| data used in refinement | 4322 |
| cutoff used in R-factor calculations | $F_o^2 > 2.0s(F_o^2)$ |
| data with I > 2.0s(I) | 3631 |
| refined extinction coef | 0.0048 |
| number of variables | 338 |
| largest shift/esd in final cycle | 0.00 |
| R(F$_o$) | 0.051 |
| R$_w$(F$_o^2$) | 0.135 |
| goodness of fit | 1.094 |

TABLE 11

Crystal data and structure refinement for the crystals of GDC-0032 Form E

| | |
|---|---|
| Empirical formula | $C_{24}H_{28}N_8O_2 \cdot C_2H_3F_3O$ |
| Formula weight | 560.59 |
| T [K] | 296(2) |
| λ [Å] | 1.540596 |
| Crystal system | Monoclinic |
| Space group | P 21/c |
| Unit cell dimensions | |
| a [Å] | 13.22417(50) |
| b [Å] | 14.89733(56) |
| c [Å] | 13.81589(34) |
| β [°] | 90.7722(18) |
| V [Å$^3$] | 2721.55 |
| Z | 4 |
| D$_c$ [g/cm$^3$] | 1.367 |
| μ [cm$^{-1}$] | 9.07021(53) |
| F(000) | 1176 |
| Capillary size [mm$^2$] | 8.0 × 0.5 |
| θ range for data collection | 2 → 25 |
| R$_{exp}$ | 0.57 |
| R$_{wp}$ | 4.34 |
| R$_p$ | 2.72 |
| R$_{Bragg}$ | 2.22 |
| GOF | 7.64 |

TABLE 12

Crystal data and structure refinement for Form F

| | |
|---|---|
| Empirical formula | $C_{24}H_{28}N_8O_2 \cdot C_2H_3N$ |
| Fw | 501.60 |
| T [K] | 296(2) |
| λ [Å] | 0.71073 |
| Crystal system | Triclinic |
| Space group | P-1 |
| Unit cell dimensions | |
| a [Å] | 10.345(2) |
| b [Å] | 11.444(2) |
| c [Å] | 12.189(3) |
| α [°] | 75.216(7) |
| β [°] | 83.063(7) |
| γ [°] | 69.876(9) |
| V [Å$^3$] | 1309.2(5) |
| Z | 2 |
| D$_c$ [g/cm$^3$] | 1.272 |
| μ [mm$^{-1}$] | 0.086 |
| F(000) | 532 |
| Crystal size [mm$^3$] | 0.40 × 0.25 × 0.20 |
| θ range for data collection [°] | 3.3 → 30 |
| Reflections collected | 11628 |
| Independent reflections | 7543 [R$_{int}$ = 0.0236] |
| Completeness to θ = 30° [%] | 98.8 |
| Max. and min. transmission | 0.9831 and 0.9666 |
| Data/restraints/parameters | 7543/0/429 |
| Goodness-of-fit on F$^2$ | 1.031 |
| Final R indices [I > 2σ(I)] | R1 = 0.0596, wR2 = 0.1477 |
| R indices (all data) | R1 = 0.0809, wR2 = 0.1661 |
| Extinction coefficient | 0.022(12) |

TABLE 13

Crystal Data and Data Collection Parameters for GDC-0032 Form H

| | |
|---|---|
| formula | $C_{24.93}H_{28.93}Cl_{2.80}N_8O_2$ |
| formula weight | 571.80 |
| space group | P 1 21/c 1 (No. 14) |
| a, Å | 14.8758(5) |
| b, Å | 14.8513(5) |
| c, Å | 13.6694(6) |
| b, deg | 111.253(8) |
| V, Å$^3$ | 2814.53(18) |
| Z | 4 |
| $d_{calc}$, g cm$^{-3}$ | 1.349 |
| crystal dimensions, mm | 0.20 × 0.12 × 0.04 |
| temperature, K | 296. |
| radiation (wavelength, Å) | Cu K$_\alpha$ alpha (1.54184) |
| monochromator | graphite |
| linear abs coef, mm$^{-1}$ | 3.128 |
| absorption correction applied | empirical$^a$ |
| transmission factors: min, max | 0.48, 0.88 |
| diffractometer | Nonius KappaCCD |
| h, k, l range | −12 to 17 −17 to 17 −13 to 16 |
| 2θ theta range, deg | 13.02-133.25 |
| mosaicity, deg | 0.90 |
| programs used | SHELXTL |
| $F_{000}$ | 1208.0 |
| weighting $1/[s^2(Fo^2) + (0.1208P)^2 + 2.3344P]$ where P = (Fo$^2$ + 2Fc$^2$)/3 data collected | 21992 |
| unique data | 3804 |
| $R_{int}$ | 0.042 |
| data used in refinement | 3804 |
| cutoff used in R-factor calculations | $F_o^2 > 2.0s(F_o^2)$ |
| data with I > 2.0s(I) | 2942 |
| refined extinction coef | 0.0014 |
| number of variables | 362 |
| largest shift/esd in final cycle | 0.00 |
| R(F$_o$) | 0.071 |
| R$_w$(F$_o^2$) | 0.209 |
| goodness of fit | 1.136 |

TABLE 14

Crystal Data for GDC-0032 Form L

| | |
|---|---|
| formula | $C_{27}H_{36}N_8O_3$ ($C_{24}H_{28}N_8O_2$ + $C_3H_8O$) |
| formula weight | 520.64 |
| space group | P 1 21/c 1 (No. 14) |
| a, Å | 13.224(3) |
| b, Å | 14.797(3) |
| c, Å | 13.603(3) |
| b, deg | 90.52(3) |
| V, Å$^3$ | 2661.7(9)) |
| Z | 4 |
| $d_{calc}$, g cm$^{-3}$ | 1.299 |
| temperature, K | 89. |
| radiation (wavelength, Å) | Synchrotron (0.7000) |
| h, k, l range | −14 to 14 −15 to 15 −15 to 15 |
| theta range, deg | 1.54-23.3 |
| programs used | SHELX97 |
| $F_{000}$ | 1016.0 |
| weighting | |
| $1/[s^2(Fo^2) + (0.0724P)^2 + 0.9585P]$ where $P = (Fo^2 + 2Fc^2)/3$ | 24329 |
| $1/[\backslash s^2(Fo^2) + (0.0493P)^2 + 1.2539P]$ where $P = (Fo^2 + 2Fc^2)/3$' data collected | |
| unique data | 3700 |
| $R_{int}$ | 0.024 |
| data used in refinement | 3700 |
| cutoff used in R-factor calculations | $F_o^2 > 2.0s(F_o^2)$ |
| data with I > 2.0s(I) | 3700 |
| refined extinction coef | 0.0123(10) |
| number of variables | 363 |
| largest shift/esd in final cycle | 0.00 |
| $R(F_o)$ | 0.036 |
| $R_w(F_o^2)$ | 0.094 |
| goodness of fit | 1.052 |

Example 7

Powder X-ray Diffraction (PXRD)

Powder X-ray diffraction patterns of samples were obtained using the Rigaku MiniFlex II® powder X-ray diffractometer. The radiation source was operated at the voltage of 30 kV and the current 15 mA. Each sample was placed in the cavity of an aluminum sample holder flattened with a glass slide to present a good surface texture and inserted into the sample holder. All samples were measured in the 2θ angle range between 2° and 40° with a scan rate of 2°/min and a step size of 0.02°.

X-ray diffraction patterns are recorded at ambient conditions in transmission geometry with a STOE STADI P diffractometer (Cu Kα radiation, primary monochromator, silicon strip detector, angular range 3° to 42° 2-theta, approximately 30 minutes total measurement time). The samples (approximately 10 to 50 mg) are prepared between thin polymer films and are analyzed without further processing (e.g. grinding or sieving) of the substance. The broad reflection at about 5.6° 2-theta is due to background noise.

XRPD analysis was also performed using a PANalytical X'Pert Pro® diffractometer. An incident beam of Cu Kα (alpha) radiation (1.54057 Å) was produced using an Optix long, fine-focus source. An elliptically graded multilayer mirror was used to focus the Cu Kα (alpha) X-rays of the source through the sample and onto the detector. The tube voltage and amperage were set to 45 kV and 40 mA, respectively. The scan range was 1.01 to 39.98° 2θ using a step size of 0.017°/minute at a scan speed of 3.3°/minute for a total collection time of 718 seconds. A silicon standard was analyzed to check the instrument alignment. The XRPD pattern consists of sharp peaks, indicating that the sample is crystalline. Representative spectra are shown in FIGS. 2, 10, 13-21.

Rigaku Rapid II image plate diffractometer equipped with a MicroMax002+ high intensity copper x-ray source.

Example 8

Differential Scanning Calorimetry (DSC)

A TA Instruments differential scanning calorimeter (Model Q100) with a mechanical cooler and a standard cell (configured the same as the sample pan) was used to measure the thermal properties of the powder samples. Each sample was loaded into a closed aluminum pan with a non-crimped lid containing zero to one pin hole and placed into the differential scanning calorimetry (DSC) cell. The cell has a nitrogen purge flowing at approximately 50 cm$^3$/min. The cell and sample were equilibrated at 20° C. The cell was then heated to 250-350° C. at 10.00° C./min while monitoring the heat flow difference between the empty reference pan and the sample pan Example 9

Thermal Gravimetric Analysis (TGA)

Weight change as a function of temperature was determined by TGA. Monitoring the sample weight, during heating in a TGA instrument (TA Instruments, model Q500), resulted in a weight vs. temperature curve. 0.1-2 milligrams of the sample were placed in a DSC pan located on the sample holder. The sample holder was heated in the TGA from 25 to 300° C. at a heating rate of 10° C. min$^{-1}$. Dry N$_2$ gas was used for purging. Isothermal experiments were conducted by heating the sample at 10° C./min to the desired temperature and then holding the sample at that temperature for at least 200 minutes.

Example 10

FT-IR

The FTIR spectra were recorded on a ThermoFisher Scientific FT-IR: Nicolet 6700.

Example 11

Dynamic Vapor Sorption (DVS)

Automated vapor sorption data were collected on a TA Instruments Q5000SA vapor sorption analyzer. NaCl and PVP were used as calibration standards. Samples were not dried prior to analysis. Adsorption and desorption data were collected at 25° C. over a range from 5 to 95% RH at 10% RH increments under a nitrogen purge. Samples were held at the corresponding RH for 1 hour prior to moving to the next RH range. Data were not corrected for the initial moisture content of the samples.

Example 12

HPLC Analytical Method

HPLC analysis was performed using an Agilent 1200SL HPLC system equipped with UV and MS detectors following the conditions presented below:

| HPLC Equipment: | LC-MS |
|---|---|
| Manufacturer: | Agilent |
| HPLC: | HP1100 |
| UV-detector: | HP DAD |
| MS-detector: | HP1100 API-ES MSD VL-type |
| Column: | Waters Sunfire ® C18 (100 × 4.6 mm; 3.5 μm). |
| Column temp: | 35° C. |
| Mobile phase: | Gradient mode |
| Mobile phase A: | 10 mM Ammonium Acetate |
| Mobile phase B: | Acetonitrile 100% |
| Flow: | 1.0 mL/min |

| Gradient: | Time [min]: | Eluent A: | Eluent B: |
|---|---|---|---|
| | 0 | 90% | 10% |
| | 5 | 10% | 90% |
| | 6 | 10% | 90% |
| | 7 | 90% | 10% |
| | 8 | 90% | 10% |

| UV-detector: | DAD |
|---|---|
| Range: | 200-400 nm |
| Wavelength: | 220 nm |
| Band width: | 4 nm |
| Time: | 0-10 min |

| MS-detector: | MSD |
|---|---|
| Scan: | positive |
| Mass Range: | 70-1000 |
| Fragmentor: | 70 |
| Time: | 0-10 min |

| Autosampler: | |
|---|---|
| Temperature: | 10° C. |
| Injection mode: | loop |
| Injection volume: | 5 μl |
| Needle wash: | 2/3; ACN/H$_2$O (v/v) |
| Dilution solvent: | Methanol |

The compound integrity is expressed as a peak-area percentage, calculated from the area of each peak in the chromatogram, except the 'injection peak', and the total peak-area. The peak-area percentage of the compound of interest is employed as an indication of the purity of the component in the sample.

Example 13

Data Collection Form B Polymorph

A colorless needle of GDC-0032 ($C_{24}H_{28}N_8O_2$) having approximate dimensions of 0.20×0.11×0.08 mm was mounted on a fiber in a random orientation. Preliminary examination and data collection were performed Cu K$_{alpha}$ radiation (1.54184 Å) on a Rigaku Rapid II® equipped with confocal optics. Refinements were performed on an LINUX PC using SHELX97® (Sheldrick, G. M. *Acta Cryst.*, (2008), A64, 112). Cell constants for data collection were obtained from least-squares refinement, using the setting angles of 18706 reflections in the range 4<q<70°. The refined mosaicity from DENZO/SCALEPACK was 0.56° indicating moderate crystal quality (Z. Otwonowski and W. Minor, Methods Enzymol (1997) 276:307). The space group was determined by the program XPREP [1]. There were no systematic absences; the space group was determined to be P-1 (#2). The data were collected at a temperature of 150 (1)K. Data were collected to a maximum 2q of 140.65°.

Data reduction: Frames were integrated with DENZO-SMN (Sheldrick, G. M. *Acta Cryst.,* 2008, A64, 112). A total of 18706 reflections were collected of which 4029 were unique. Lorentz and polarization corrections were applied to the data. The linear absorption coefficient is 7.25/mm for Cu K$_a$ radiation. An empirical absorption correction using SCALEPACK was applied. Transmission coefficients ranged from 0.90 to 0.94. Intensities of equivalent reflections were averaged. The agreement factor for the averaging was 4.2% based on intensity. The triclinic cell parameters and calculated volume are: a=9.7944(14), b=10.4767(11), c=12.5994(17) Å, α=96.145(10), β=95.749(11), β=115.072 (9)°, V=1149.0(3) Å$^3$. For Z=2 and F.W.=460.54, the calculated density is 1.331 g/cm$^3$.

Structure Solution and Refinement: The structure was solved by direct methods using SIR2004 (M. C. Burla, et al, *J. Appl. Crystalogr.*, (2005) 38:381). The remaining atoms were located in succeeding difference Fourier syntheses. Hydrogen atoms were included in the refinement but restrained to ride on the atom to which they are bonded. The structure was refined in full-matrix least-squares where the function minimized was.

Refinement was performed on a LINUX PC using SHELX-97.

$$\Sigma w(|Fo|^2-|Fc|^2)^2$$

The weight w is defined as $1/[s^2(Fo^2)+(0.0810P)^2+0.5152P]$ where $P=(Fo^2+2Fc^2)/3$. Scattering factors were taken from the "International Tables for Crystallography" ("International Tables for Crystallography", Vol. C, Kluwer Academic Publishers, Utrecht, The Netherlands, (1992), Tables 4.2.6.8 and 6.1.1.4.). 4029 reflections were used in the refinements. However, only the 3257 reflections with $F_o^2 > 2\sigma(F_o^2)$ were used in calculating R1. The final cycle of refinement included 330 variable parameters and converged (largest parameter shift was <0.01 times its estimated standard deviation with unweighted and weighted agreement factors of:

$$R = \Sigma |F_o - F_c| / \Sigma F_o = 0.060$$

$$R_w = \sqrt{(\Sigma w(F_o^2 - F_c^2)^2 / \Sigma w(F_o^2)^2)} = 0.158$$

The goodness-of-fit parameter was 1.061. The highest peak in the final difference Fourier had a height of 0.41 e/Å$^3$. The minimum negative peak had a height of −0.33 e/Å$^3$.

Calculated X-ray Powder Diffraction (XRPD) Pattern: A calculated XRPD pattern was generated for Cu radiation using Mercury 2.3 (Mercury CSD2.3 (Build RC4), ICDD, 2009) and the atomic coordinates, space group, and unit cell parameters from the single crystal data. Since the single crystal data are collected at low temperatures (150 K) some shifting between the calculated and experimental powder diffraction pattern is expected. Typically this shifting is a function of 2θ (theta), but since the thermal contraction of the crystal is not known, this may not be the case.

ORTEP and Packing Diagrams: prepared using ORTEP III (Johnson, C. K. ORTEPIII, Report ORNL-6895, Oak Ridge National Laboratory, TN, U.S.A. (1996). OPTEP-3 for Windows V1.05, Farrugia, L. J., *J. Appl. Crystalogr.* (1997), 30:565) program within the PLATON (Spek, A. L. *PLATON. Molecular Graphics Program.* Utrecht University, Utrecht, The Netherlands, (2008); Spek, A. L, *J. Appl. Crystalogr.* (2003), 36:7) software package. Atoms are represented by 50% probability anisotropic thermal ellipsoids. Packing diagrams were prepared using Mercury visualization software. Hydrogen bonding is represented as dashed lines.

X-ray powder diffraction (XRPD): The XRPD pattern was collected at SSCI, a division of Aptuit, using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop and short anti-scattering were used to minimize the background generated by air scattering. Soller slits were used for the incident and diffracted beams to minimize axial divergence. The diffraction pattern was collected using a scanning position-sensitive detector (X'Celerator) located 240 mm from the specimen. The data acquisition parameters of the diffraction pattern are displayed above the image of the pattern in the Data section. Prior to the analysis a silicon specimen (NIST standard reference material 640c) was analyzed to verify the position of the silicon 111 peak.

TABLE 15

Reflection assignments in degrees two theta:

Form A: 5.62, 9.88, 10.14, 14.09, and 16.26
Form B: 9.40, 10.84, 16.72, 18.7, and 26.60
Form C: 6.16, 8.56, 13.76, 18.52, and (21.66 or 26.82)
Form D: 12.08, 15.36, 17.48, 17.66, and 19.44
Form E: 6.70, 8.96, 13.66, 15.94, and 18.72
Form F: 7.52, 9.13, 13.99, 15.07, and 18.30
Form H: 6.39, 8.74, 13.54, 13.82, and 19.23
Form J: 5.12, 8.74, 10.82, 14.62, and 17.42
Form K: 10.99, 17.01, 20.28, 22.56, and 25.92
Form L: 6.61, 8.90, 15.92, 18.42, and 25.76
Form M: 7.47, 8.88, 14.95, 17.78, and 20.01
Form N: 7.48, 9.22, 14.98, 18.48, and 24.34
Form O: 6.28, 13.48, 13.90,, 18.02, 18.64, and 25.68
Form P: 7.46, 8.89, 14.96, 17.82, and 24.18
Form Q: 9.82, 17.70, 20.76, 20.96, and 24.08
Form R: 7.36, 8.84, 14.72, 17.71, and 24.1
Form S: 8.79, 10.63, 13.26, and 26.25
Form T: 6.54, 8.85, 13.53, 17.98, and 25.70
Form U: 6.36, 8.69, 13.48, 20.12, and 25.70
Form V: 6.18, 8.60, 13.84, 17.38, and 18.47
Form W: 5.96, 7.60, 11.92, 22.80, and 26.52
Form X: 10.12, 14.14, 16.28, 20.59, and 23.24
Form Y: 6.01, 10.12, 14.24, 16.30, and 20.40
Form Z: 5.76, 8.29, 13.25, 13.62, and 25.94
Form AA: 12.02, 16.65, 18.92, 21.13, and 26.39
Form AB: 5.82, 6.54, 9.38, and 26.34
Form AC: 6.32, 8.74, 13.58, 13.88, and 25.84

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A process for preparing a crystalline polymorph comprising heating a slurry of (2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide in isoamyl alcohol and then cooling the mixture whereby a Form B crystalline polymorph that exhibits an X-ray powder diffraction pattern having characteristic peaks expressed in degrees 2-theta at approximately 10.7, 14.0, 16.4, 18.6, 22.1, and 26.4 is formed.

2. The process of claim 1 wherein the Form B polymorph is characterized by the X-ray powder diffraction pattern shown in FIG. 10.

3. A process for preparing a crystalline polymorph comprising mixing (2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide with an aqueous alcohol solvent comprising water and an alcohol selected from the group consisting of n-butanol and n-propanol, whereby a crystalline, mono-hydrate polymorph of (2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide designated the Form D polymorph is formed that exhibits an X-ray powder diffraction pattern having characteristic peaks expressed in degrees 2-theta at approximately 12.2, 17.5, 17.7, 18.3, 20.1, 21.3, 22.8, and 26.0.

4. The process of claim 3 wherein the Form D polymorph is characterized by the X-ray powder diffraction pattern shown in FIG. 14.

* * * * *